(12) United States Patent
Desai et al.

(10) Patent No.: US 8,846,771 B2
(45) Date of Patent: *Sep. 30, 2014

(54) COMPOSITIONS AND METHODS OF DELIVERY OF PHARMACOLOGICAL AGENTS

(71) Applicant: Abraxis BioScience, LLC, Los Angeles, CA (US)

(72) Inventors: Neil P. Desai, Los Angeles, CA (US); Patrick Soon-Shiong, Los Angeles, CA (US); Vuong Trieu, Calabasas, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/649,987

(22) Filed: Oct. 11, 2012

(65) Prior Publication Data

US 2013/0244952 A1 Sep. 19, 2013

Related U.S. Application Data

(63) Continuation of application No. 13/038,287, filed on Mar. 1, 2011, now Pat. No. 8,314,156, which is a continuation of application No. 12/758,413, filed on Apr. 12, 2010, now Pat. No. 7,923,536, which is a continuation of application No. 11/553,339, filed on Oct. 26, 2006, now Pat. No. 7,820,788, which is a continuation of application No. 10/731,224, filed on Dec. 9, 2003, now abandoned.

(60) Provisional application No. 60/432,317, filed on Dec. 9, 2002, provisional application No. 60/526,544, filed on Dec. 3, 2003, provisional application No. 60/526,773, filed on Dec. 4, 2003, provisional application No. 60/527,177, filed on Dec. 5, 2003.

(51) Int. Cl.

| | | |
|---|---|---|
| A61K 47/42 | (2006.01) |
| A61K 9/14 | (2006.01) |
| A61K 9/51 | (2006.01) |
| C07K 14/76 | (2006.01) |
| A61P 35/00 | (2006.01) |
| A61K 31/164 | (2006.01) |
| A61K 31/436 | (2006.01) |
| A61K 9/00 | (2006.01) |
| A61K 31/343 | (2006.01) |
| A61K 47/18 | (2006.01) |
| B82Y 5/00 | (2011.01) |
| A61K 31/337 | (2006.01) |
| A61K 9/107 | (2006.01) |
| A61K 31/165 | (2006.01) |
| A61K 31/355 | (2006.01) |
| A61K 9/19 | (2006.01) |
| A61K 31/198 | (2006.01) |
| A61K 31/16 | (2006.01) |
| A61K 31/05 | (2006.01) |
| A61K 38/13 | (2006.01) |
| A61K 31/4745 | (2006.01) |
| A61K 31/427 | (2006.01) |
| A61K 31/7048 | (2006.01) |

(52) U.S. Cl.
CPC .............. *A61K 47/42* (2013.01); *A61K 31/164* (2013.01); *Y10S 977/911* (2013.01); *A61K 31/436* (2013.01); *Y10S 977/906* (2013.01); *A61K 9/0078* (2013.01); *A61K 31/343* (2013.01); *A61K 47/18* (2013.01); *A61K 9/146* (2013.01); *B82Y 5/00* (2013.01); *A61K 31/337* (2013.01); *A61K 9/1075* (2013.01); *Y10S 977/779* (2013.01); *Y10S 977/705* (2013.01); *A61K 31/165* (2013.01); *A61K 31/355* (2013.01); *A61K 9/19* (2013.01); *A61K 31/198* (2013.01); *A61K 31/16* (2013.01); *A61K 9/0019* (2013.01); *A61K 31/05* (2013.01); *A61K 38/13* (2013.01); *Y10S 977/773* (2013.01); *A61K 31/4745* (2013.01); *A61K 31/427* (2013.01); *A61K 31/7048* (2013.01)
USPC .......... 514/776; 514/19.3; 424/489; 424/499; 530/362; 977/911; 977/906; 977/779; 977/705; 977/773

(58) Field of Classification Search
None
See application file for complete search history.

(56) References Cited

U.S. PATENT DOCUMENTS

| | | |
|---|---|---|
| 4,425,319 A | 1/1984 | Yokoyama et al. |
| 4,645,660 A | 2/1987 | Takahashi et al. |
| 5,118,528 A | 6/1992 | Fessi et al. |
| 5,133,908 A | 7/1992 | Stainmesse et al. |

(Continued)

FOREIGN PATENT DOCUMENTS

| | | |
|---|---|---|
| CN | 1355005 A | 6/2002 |
| EP | 0 227 593 A1 | 7/1987 |

(Continued)

OTHER PUBLICATIONS

Altmayer, P. et al. (1995). "Propofol Binding to Human Blood Proteins," *Arzneimittel Forschung Drug Research* 45(II)(10):1053-1056.

(Continued)

*Primary Examiner* — Marsha Tsay
(74) *Attorney, Agent, or Firm* — Morrison & Foerster LLP.

(57) ABSTRACT

The present invention relates to a pharmaceutical composition comprising a pharmaceutical agent and a pharmaceutically acceptable carrier, which carrier comprises a protein, for example, human serum albumin and/or deferoxamine. He human serum albumin is present in an amount effective to reduce one or more side effects associated with administration of the pharmaceutical composition. The inventor also provides methods for reducing on or more side effects of administration of the pharmaceutical composition, and methods for enhancing transport and binding of a pharmaceutical agent to a cell.

12 Claims, No Drawings

(56) References Cited

U.S. PATENT DOCUMENTS

| | | |
|---|---|---|
| 5,272,171 A | 12/1993 | Ueda et al. |
| 5,362,478 A | 11/1994 | Desai et al. |
| 5,399,363 A | 3/1995 | Liversidge et al. |
| 5,439,686 A | 8/1995 | Desai et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,616,330 A | 4/1997 | Kaufman et al. |
| 5,626,862 A | 5/1997 | Brem et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,651,986 A | 7/1997 | Brem et al. |
| 5,665,382 A | 9/1997 | Grinstaff et al. |
| 5,665,383 A | 9/1997 | Grinstaff et al. |
| 5,681,846 A | 10/1997 | Trissel |
| 5,714,520 A | 2/1998 | Jones et al. |
| 5,716,981 A | 2/1998 | Hunter et al. |
| 5,731,355 A | 3/1998 | Jones et al. |
| 5,731,356 A | 3/1998 | Jones et al. |
| 5,886,026 A | 3/1999 | Hunter et al. |
| 5,916,596 A | 6/1999 | Desai et al. |
| 5,945,033 A | 8/1999 | Yen |
| 5,977,163 A | 11/1999 | Li et al. |
| 5,990,153 A | 11/1999 | Wood et al. |
| 5,994,341 A | 11/1999 | Hunter et al. |
| 5,997,904 A | 12/1999 | Magdassi et al. |
| 6,028,108 A | 2/2000 | George |
| 6,096,331 A | 8/2000 | Desai et al. |
| 6,100,302 A | 8/2000 | Pejaver et al. |
| 6,120,805 A | 9/2000 | Spenlehauer et al. |
| 6,143,276 A | 11/2000 | Unger |
| 6,147,122 A | 11/2000 | Mirejovsky et al. |
| 6,150,423 A | 11/2000 | Carpenter |
| 6,177,477 B1 | 1/2001 | George et al. |
| 6,197,051 B1 | 3/2001 | Zhong |
| 6,197,349 B1 | 3/2001 | Westesen et al. |
| 6,204,054 B1 | 3/2001 | Sutton et al. |
| 6,306,993 B1 | 10/2001 | Rothbard et al. |
| 6,310,039 B1 | 10/2001 | Kratz |
| 6,326,406 B1 | 12/2001 | De Tommaso |
| 6,362,234 B1 | 3/2002 | Hendler |
| 6,399,087 B1 | 6/2002 | Zhang et al. |
| 6,441,025 B2 | 8/2002 | Li et al. |
| 6,458,373 B1 | 10/2002 | Lambert et al. |
| 6,469,069 B1 | 10/2002 | Mirejovsky et al. |
| 6,506,405 B1 | 1/2003 | Desai et al. |
| 6,528,067 B1 | 3/2003 | Magdassi et al. |
| 6,537,579 B1 | 3/2003 | Desai et al. |
| 6,565,842 B1 | 5/2003 | Sojomihardo et al. |
| 6,652,884 B2 | 11/2003 | Falciani |
| 6,743,826 B1 | 6/2004 | Hegedus et al. |
| 6,749,868 B1 | 6/2004 | Desai et al. |
| 6,753,006 B1 | 6/2004 | Desai et al. |
| 6,759,431 B2 | 7/2004 | Hunter et al. |
| 7,119,124 B2 | 10/2006 | Hegedus et al. |
| 7,332,568 B2 | 2/2008 | Trieu et al. |
| 7,758,891 B2 | 7/2010 | Desai et al. |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Desai et al. |
| 8,314,156 B2 | 11/2012 | Desai et al. |
| 2003/0185894 A1 | 10/2003 | Zenoni et al. |
| 2003/0187062 A1 | 10/2003 | Zenoni et al. |
| 2003/0199425 A1 | 10/2003 | Desai et al. |
| 2004/0131692 A1 | 7/2004 | Kreuter et al. |
| 2005/0004002 A1 | 1/2005 | Desai et al. |
| 2005/0009731 A1 | 1/2005 | Desai et al. |
| 2005/0064028 A1 | 3/2005 | Hegedus et al. |
| 2006/0263434 A1 | 11/2006 | Desai et al. |
| 2007/0082838 A1 | 4/2007 | De et al. |
| 2007/0087022 A1 | 4/2007 | Desai et al. |
| 2007/0093547 A1 | 4/2007 | Desai et al. |
| 2007/0116774 A1 | 5/2007 | Desai et al. |
| 2007/0117133 A1 | 5/2007 | Trieu et al. |
| 2007/0129448 A1 | 6/2007 | Desai et al. |
| 2007/0166388 A1 | 7/2007 | Desai et al. |
| 2008/0063724 A1 | 3/2008 | Desai et al. |
| 2008/0280987 A1 | 11/2008 | Desai et al. |
| 2009/0048331 A1 | 2/2009 | Soon-Shiong et al. |
| 2009/0098210 A1 | 4/2009 | Desai et al. |
| 2009/0196933 A1 | 8/2009 | De et al. |
| 2009/0263483 A1 | 10/2009 | Desai et al. |
| 2009/0304805 A1 | 12/2009 | Desai et al. |
| 2010/0035800 A1 | 2/2010 | Desai et al. |
| 2010/0048499 A1 | 2/2010 | Desai et al. |
| 2010/0112077 A1 | 5/2010 | Desai et al. |
| 2010/0166869 A1 | 7/2010 | Desai et al. |
| 2010/0183728 A1 | 7/2010 | Desai et al. |
| 2010/0196490 A1 | 8/2010 | Desai et al. |
| 2010/0215751 A1 | 8/2010 | Desai et al. |
| 2010/0297243 A1 | 11/2010 | Desai et al. |
| 2011/0052708 A1 | 3/2011 | Soon-Shiong et al. |
| 2011/0118342 A1 | 5/2011 | De et al. |
| 2011/0151012 A1 | 6/2011 | Desai et al. |
| 2011/0165256 A1 | 7/2011 | Desai et al. |
| 2011/0196026 A1 | 8/2011 | De et al. |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |

FOREIGN PATENT DOCUMENTS

| | | |
|---|---|---|
| EP | 0 349 428 A1 | 1/1990 |
| EP | 0 544 292 A2 | 6/1993 |
| EP | 0 544 292 A3 | 6/1993 |
| FR | 2 775 900 A1 | 9/1999 |
| RU | 2127606 C1 | 3/1999 |
| WO | WO-92/07259 A1 | 4/1992 |
| WO | WO-94/13300 A1 | 6/1994 |
| WO | WO-94/18954 A1 | 9/1994 |
| WO | WO-94/20072 A1 | 9/1994 |
| WO | WO-95/03036 A1 | 2/1995 |
| WO | WO-96/40829 A1 | 12/1996 |

(56) References Cited

FOREIGN PATENT DOCUMENTS

| | | |
|---|---|---|
| WO | WO-97/10850 A1 | 3/1997 |
| WO | WO-98/07410 A1 | 2/1998 |
| WO | WO-98/14174 A1 | 4/1998 |
| WO | WO-98/14175 A1 | 4/1998 |
| WO | WO-99/00113 A1 | 1/1999 |
| WO | WO-99/13914 A1 | 3/1999 |
| WO | WO-99/39696 A1 | 8/1999 |
| WO | WO-00/06152 A1 | 2/2000 |
| WO | WO-00/23117 A1 | 4/2000 |
| WO | WO-00/64437 A1 | 11/2000 |
| WO | WO-00/71079 A2 | 11/2000 |
| WO | WO-01/12229 A1 | 2/2001 |
| WO | WO-01/49268 A1 | 7/2001 |
| WO | WO-01/89522 A1 | 11/2001 |
| WO | WO-02/087545 A1 | 11/2002 |
| WO | WO-02/089776 A1 | 11/2002 |
| WO | WO-03/096944 A1 | 11/2003 |
| WO | WO-2004/007520 A2 | 1/2004 |
| WO | WO-2004/007520 A3 | 1/2004 |
| WO | WO-2004/052401 A2 | 6/2004 |
| WO | WO-2004/052401 A3 | 6/2004 |
| WO | WO-2006/034147 A2 | 3/2005 |
| WO | WO-2006/034147 A3 | 3/2005 |
| WO | WO-2005/117952 A2 | 12/2005 |
| WO | WO-2005/117952 A3 | 12/2005 |
| WO | WO-2006/089207 A1 | 8/2006 |

OTHER PUBLICATIONS

Awada, A. (2002) "New Cytotoxic Agents and Molecular-Targeted Therapies in the Treatment of Metastatic Breast Cancer," *Trends in Experimental and Clinical Medicine* 12:4-15.

Awada, A. et al. (2003). "The Pipeline of New Anticancer Agents for Breast Cancer Treatment in 2003," *Critical Reviews in Oncology/Hematology* 48:45-63.

Bayés, M. et al. (May 2003). "Gateways to Clinical Trials," *Methods and Findings in Experimental and Clinical Pharmacology* 25(4):317-340.

Becher (1965). *Emulsions: Theory and Practice*, 2nd edition, American Chemical Society, Monograph Series, Reinhold Publishing Corporation, New York, USA, Table of Contents on p. xi, for a total of 3 pages.

Bielen, S. J. et al. (1996). "The Effect of a Cyclodextrin Vehicle on the Cardiovascular Profile of Propofol in Rats," *Anest. Analg.* 82:920-924.

Briggs, L.P. et al. (1982). "An Adverse Reaction to the Administration of Disoprofol (Diprivan)," *Anaesthesia* 37(7):1099-1101.

Calabresi, P. et al. (1996). Introduction of "Chemotherapy of Neoplastic Disease," Section X in *The Pharmacological Basis of Therapeutics*, 9th ed., McGraw-Hill: New York, pp. 1225-1230.

Campbell, K. J. et al. (Jul. 2003). "A Phase I Trial of ABI-007 Administered Weekly for Three Doses Every 4 Weeks in Patients With Advanced Non-Hematologic Malignancies," *Proceedings of the American Association for Cancer Research* held on Jul. 11-14, 2003, Washington Convention Center, Washington, D. C., vol. 44($2^{nd}$ edition), p. 1059, abstract No. R5337.

Carter, D.C. et al. (1994). "Structures of Serum Albumin," *Advances in Protein Chemistry*. Schumaker, V.N., ed., Academic Press, Inc.: San Diego, CA, 45:153-203.

Chuang, V. T. G. et al. (May 2002). "Pharmaceutical Strategies Utilizing Recombinant Human Serum Albumin," *Pharmaceutical Research* 19(5):569-577.

Curry et al. (Sep. 1998). "Crystal Structure of Human Serum Albumin Complexed with Fatty Acid Reveals an Asymmetric Distribution of Binding Sites," *Nat. Struct. Biol* 5(9):827-835.

Curry, S. et al. (Nov. 23, 1999). "Fatty Acid Binding to Human Serum Albumin: New Insights From Crystallographic Studies," *Biochim. Biophys. Acta.* 1441(2-3):131-140.

Damascelli, B. et al. (Nov. 15, 2001). "Intraarterial Chemotherapy with Polyoxyethylated Castor Oil Free Paclitaxel Incorporated in Albumin Nanoparticles (ABI-007)," *Cancer* 92(10):2592-2602.

Damascelli, B. et al. (Jul. 2003). "A Novel Intraarterial Chemotherapy Using Paclitaxel in Albumin Nanoparticles to Treat Advanced Squamous Cell Carcinoma of the Tongue: Preliminary Findings," *AJR Am. J. Roentgenol.* 181(1):253-260.

Davies, A.F. et al. (Jun. 2002). "Efficacy of Microfiltration in Decreasing Propofol-Induced Pain," *Anaesthesia* 57(6):557-561.

Desai, N.P. et al. (Apr. 1994). "Controlled and Targeted Drug Delivery With Biocompatible Protein Shell Microspheres," *The 20th Annual Meeting of the Society for Biomaterials*, Boston, MA, Apr. 5-9, 1994, p. 112.

Desai, N.P. et al. (Oct.-Nov. 1994). "Intravenous Targeted Delivery of Chemo-therapeutic Agents in Protein Microspheres," *XVI International Cancer Progress*, New Delhi, India, Oct. 30-Nov. 5, 1994, p. 275.

Desai, N.P. et al. (Mar. 1995). "In Vivo Drug Delivery With Biocompatible Protein Shell Microspheres," *The 21st Annual Meeting of the Society for Biomaterials*, San Francisco, CA Mar. 18-22, 1995, one page.

Desai, N.P. et al. (Aug. 1995). "Protein Microcapsules as Drug Delivery Vehicles," *26th Annual Meeting of the Fine Particle Society*, Chicago, IL, Aug. 22-25, 1995, one page.

Desai, N.P. et al. (Apr.-May 1997). "Protein-Stabilized Nanoparticles as Drug Delivery Vehicles," *Transactions: 23rd Annual Meeting of the Society for Biomaterials*, New Orleans, LA, Apr. 30-May 4, 1997, 20:172.

Desai, N.P. et al. (Apr. 1998). "Protein Based Nanoparticle Delivery Systems," *28th Annual Meeting of the Fine Particle Society*, Dallas, TX, Apr. 1-3, 1998, one page.

Desai, N.P. et al. (May 2000). "Protein-Based Nanoparticles for Drug Delivery of Paclitaxel," Transactions of the Sixth World Biomaterials Congress, Kamuela, HI, May 15-20, 2000, III(I):199 (one page).

Desai, N. P. et al. (2002). "Evidenced of Enhanced In Vivo Efficacy at Maximum Tolerated Dose (MTD) of Nanoparticle Paclitaxel (ABI-007) and Taxol in 5 Human Tumor Xenografts of Varying Sensitivity to Paclitaxel," 2002 ASCO Annual Meeting American Society of Clinical Oncology, Orlando, Florida, May 2002, *Proc. Am. Soc. Clin. Oncol* 21:Abstract No. 462, 4 pages.

Desai, N. et al. (Dec. 2002). "Evidence of a Novel Transporter Mechanism for a Cremophor-Free, Protein-Engineered Paclitaxel (ABI-007) and In Vivo Antitumor Activity in MX-1 Human Breast Tumor Xenograft Model," *Breast Cancer Research and Treatment*, $25^{th}$ Annual San Antonio Breast Cancer Symposium (SABCS), San Antonio, Texas, 76(Suppl. 1) Abstract No. 524, p. S131.

Desai, N. et al. (Dec. 2002). "Preclinical and Clinical Pharmacokinetics and Safety of ABI-007, a Novel, Cremophor-Free, Protein-Engineered Nanotransfer of Paclitaxel," *Breast Cancer Research and Treatment*, $25^{th}$ Annual San Antonio Breast Cancer Symposium (SABCS), San Antonio, Texas 76(Suppl. 1) Abstract No. 523, p. S131.

Desai, N. et al. (Jul. 2003). "Oral Bioavailability of Paclitaxel in a Novel, Cremophor el-Free, Protein-Based Nanoparticle Preparation," *Proceedings of the American Association of Cancer Research* (AACR) $94^{th}$ Annual Meeting, Jul. 11-14, 2003, Washington Convention Center, Washington D.C. 44($2^{nd}$ edition), Abstract No. 3673, p. 732.

Desai, N. et al. (Jul. 2003). "Pulmonary Delivery of a Novel, Cremophor-Free, Protein-Based Nanoparticle Preparation of Paclitaxel," *Proceedings of the American Association for Cancer Research* 44($2^{nd}$ edition), Abstract No. 3672, p. 731.

Desai, N. et al. (Dec. 2003). "Evidence of Greater Antitumor Activity and Red Cell Partitioning and Superior Antitumor Activity of Cremophor Free Nanoparticle Paclitaxel (ABI-007) Compared to Taxol," *Breast Cancer Research and Treatment*, $26^{th}$ Annual San Antonio Breast Cancer Symposium (SABCS), San Antonio, Texas, 82(Supp. 1): Abstract No. 348, pp. S82-S83.

Desai, N. et al. (Dec. 2003). "Evidence of Greater Antitumor Activity of Cremophor®-Free Nanoparticle Albumin-Bound (*nab*) Paclitaxel (Abraxane) Compared to Taxol: Role of a Novel Albumin Transporter Mechanism," Poster presented at $26^{th}$ Annual San Antonio Breast Cancer Symposium (SABCS) held on Dec. 3-6, 2003, San Antonio, Texas, one page (Poster).

Desai, N. et al. (Feb. 15, 2006). "Increased Antitumor Activity, Intratumor Paclitaxel Concentrations, and Endothelial Cell Transport

(56) References Cited

OTHER PUBLICATIONS of Cremophor-Free, Albumin-Bound Paclitaxel, ABI-007, Compared With Cremophor-Based Paclitaxel," *Clin. Cancer Res.* 12(4):1317-1324.
Doenicke, A.W. et al. (1996). "Reducing Pain During Propofol Injection: The Role of the Solvent," *Anesthesia & Analgesia* 82:472-474.
Dosio, F. et al. (1997). "Preparation, Characterization and Properties In Vitro and In Vivo of a Paclitaxel-Albumin Conjugate," *J. Cont. Rel.* 47:293-304.
drugs.com (Jun. 22, 2004). "Deferoxamine (Systemic)," located at <http://www.drugs.com/MMX/Deferoxamine_Mesylate.html>, last accessed Feb. 4, 2005, nine pages.
Eggling, S. (2003). "Variation on Percentage Concentration Weight/Volume Percent or Mass/Volume Percent," located at http://dl.clackamas.cc.or.us/ch105-04/wtvolpct.htm>, last visited on Feb. 4, 2005, one page.
Erlich, R. et al. (Jun. 2002). "American Society of Clinical Oncology—38th Annual Meeting, May 18-21, 2002, Orlando, FL, USA," *Investigational Drugs Journal* 5(6):497-502.
Fehske, K. J. et al. (Jan. 1, 1981). "The Location of Drug Binding Sites in Human Serum Albumin," *Biochemical Pharmacology* 30(7):687-692.
Finlayson, J.S. (1980). "Albumin Products," *Seminars in Thrombosis and Hemostasis*, Mammen, E. F. (ed.), Stratton Intercontinental Medical Book Corporation, New York, NY, 6(2):85-120.
Flournoy, D.J. (Jul. 1991). "In Vitro Antimicrobial Properties of Deferoxamine Mesylate," *Eur. J. Clin. Microbiol. Infect. Dis* 10(7):597-598.
Garrido, M.J. et al. (1994). "Caracterización de la Fijación de Propofol a las Proteínas Plasmáticas y Posibles Interacciones," *Rev. Esp. Anestesiol. Reanim.* 41(6):308-312, with English abstract (one page).
Gelderblom, H. et al. (Sep. 2001). "Cremophor EL: the Drawbacks and Advantages of Vehicle Selection for Drug Formulation," *Eur. J. Cancer* 37(13):1590-1598.
Gradishar, W. J. et al. (Nov. 1, 2005). "Phase III Trial of Nanoparticle Albumin-Bound Paclitaxel Compared with Polyethylated Castor Oil-Based Paclitaxel in Women With Breast Cancer," *J. Clin. Oncol.* 23(31):7794-7803.
Green, M. R. et al. (Aug. 2006, e-pub. Jun. 1, 2006). "Abraxane® A Novel Cremophor-Free, Albumin-Bound Particle Form of Paclitaxel for the Treatment of Advanced Non-Small-Cell Lung Cancer," *Ann. Oncol.* 17(8):1263-1268.
Grinstaff, M.W. et al. (Mar. 1994). "Intravenous Targeted Delivery of Taxol in Protein Microspheres," *Abstracts of Papers 207th National Meeting of the American Chemical Society*, 1994, San Diego, CA, Mar. 13-17, 1994, 207(1-2), Abstract No. 91, one page.
Gutteridge, J.M.C. et al. (1981). "Iron-Dioxygen-Dependent Changes to the Biological Activities of Bleomycin," *J. Inorg. Biochem.* 15:349-357.
Gutteridge, J.M.C. (1984). "Streptonigrin-Induced Deoxyribose Degradation: Inhibition by Superoxide Dismutase, Hydroxyl Radical Scavengers and Iron Chelators," *Biochem. Pharm.* 33(19):3059-3062.
Halliwell, B. (1989). "Protection Against Tissue Damage in Vivo by Desferrioxamine: What is Its Mechanism of Action?" *Free Radic. Biol. Med.* 7(6):645-651.
Hauser, C.J. et al. (Jun. 1980). "Oxygen Transport Responses to Colloids and Crystalloids in Critically Ill Surgical Patients," *Surgery, Gynecology and Obstetrics* 150(6):811-816.
Hawkins, M. J. et al. (2004). "Rationale, Preclinical Support, and Clinical Proof-of-Concept for Delivery of Water-Insoluble Therapeutics by a Novel Nanoparticle Albumin-Bound (Nab) Technology: Experience With Paclitaxel," *Cancer Invest.* 22(Suppl. 1):viii-xxvii, 1-111. Abstracts from the Chemotherapy Foundation Symposium XXI: Innovative Cancer Therapy for Tomorrow, Nov. 12-15, 2003, New York, New York, USA, vol. 22, Supplement 1, pp. 99-100, Abstract No. 79.
He, X.M. et al. (Jul. 16, 1992). "Atomic Structure and Chemistry of Human Serum Albumin," *Nature* 358(6383):209-215.

HealthTouch® Online. (2000). "Deferoxamine (Systemic)," located at <http://healthtouch.com>, 5 pages.
Ibrahim, N.K. et al. (2000). "Phase I Study of Cremophor-Free, Protein-Stabilized, Nanoparticle Formulation of Paclitaxel (Abi-007) in Solid Tumors," Abstract 609F in *Proceedings of Thirty-Sixth Annual Meeting of the American Society of Clinical Oncology*, New Orleans, Louisiana, May 20-23, 2000, p. 155a, Abstract No. 609F.
Ibrahim, N. K. et al. (May 2002). "Phase I and Pharmacokinetic Study of ABI-007, a Cremophor-Free, Protein-Stabilized, Nanoparticle Formulation of Paclitaxel," *Clin. Cancer Res.* 8(5):1038-1044.
Ibrahim, N. K. et al. (Dec. 2002). "Efficacy and Dose-Dependent Activity of ABI-007, a Cremophor-Free Nanoparticle Paclitaxel, in First-Line Metastatic Breast Cancer: Integrated Results of 2 Phase II Trials," *Breast Cancer Research and Treatment, 25th Annual San Antonio Breast Cancer Symposium*, 76(Suppl. 1): Abstract No. 522, p. S131.
Ibrahim, N. K. et al. (Sep. 1, 2005). "Multicenter Phase II Trial of ABI-007, an Albumin-Bound Paclitaxel, in Women With Metastatic Breast Cancer," *J. Clin. Oncol.* 23(25):6019-6026.
John, M. C. et al. (Mar. 6, 2002). "A Novel Preparation of Systemic Paclitaxel Reduces In-Stent Restenosis in the Rabbit," *Journal of the American College of Cardiology, Abstracts—ACCIS2002 (Angiography & Interventional Cardiology)* Abstract No. 1005-6, p. 5A.
Juven, B.J. et al. (1994). "Factors that Interact with the Antibacterial Action of Thyme Essential Oil and its Active Constituents," *J. Appl. Bacteriol.* 76(6):626-631.
Klebanoff, S.J. et al. (Nov. 25, 1989). "Oxygen-based Free Radical Generation by Ferrous Ions and Deferoxamine," *J. Bio. Chem.* 264(33):19765-19771.
Knibbe, C.A.J. et al. (1999). "Pharmacokinetics, Induction of Anaesthesia and Safety Characteristics of Propofol 6% SAZN vs Propofol 1% SAZN and Diprivan®-10 after Bolus Injection," *Br. J. Clin. Pharmacol.* 47(6):653-660.
Kolodgie, F. D. et al. (Sep. 3, 2002). "Sustained Reduction of In-Stent Neointimal Growth With The Use of a Novel Systemic Nanoparticle Paclitazel," *Circulation* 106:1195-1198.
Kovár, J. et al. (Mar. 2000). "Unexpected Effects of Albumin on Apoptosis Induction by Deferoxamine In Vitro," *In Vitro Cell Dev. Biol. Anim.* 36(3):151-152.
Kragh-Hansen, U. (1990). "Structure and Ligand Binding Properties of Human Serum Albumin," *Dan. Med. Bull.* 37(1):57-84.
Kuenen, B.C. (Mar. 15, 2002). "Dose-Finding and Pharmacokinetic Study of Cisplatin, Gemcitabine, and SU5416 in Patients With Solid Tumors," *J. Clin. Oncol.* 20(6):1657-1667.
Lanocita, R. et al. (2000). "A Novel Intra-Arterial Chemotherapeutic Approach of Squamous Cell Cancer of Head and Neck Using High Dose Cremaphore, Free Paclitaxel/Albumin Nanoparticles (ABI-007)," *Annals of Oncology, Second National Congress of Medical Oncology*, Oct. 28-31, 2000, Genova, Italy, vol. 11, Supplement 2, Poster Session A, Abstract No. A26, p. 7.
Lanocita, R. et al. (Nov. 2000). "High Dose of Cremophore-Free Paclitaxel/Albumine Nanoparticles (ABI-007) for a Novel Intra-Arterial Approach to Squamous Cell Cancer of Head and Neck," *2000 Scientific Program, Radiological Society of North America, RSNA 2000, Explore, 86th Scientific Assembly and Annual Meeting*, Nov. 26-Dec. 1, 2000, McCormick Place, Chicago, Illinois, vol. 217, p. 288, Abstract No. 366.
Lanocita, R. et al. (Nov. 2000). "Squamous Cancer of Anal Canal: Intra-Arterial Chemotherapeutic Approach Using High Dose of Cremaphore-Free Paclitaxel/Albumin Nanoparticles (ABI-007)," *2000 Scientific Program, Radiological Society of North America, RSNA 2000, Explore, 86th Scientific Assembly and Annual Meeting*, Nov. 26-Dec. 1, 2000, McCormick Place, Chicago, Illinois, vol. 217, p. 504, Abstract No. 1244.
Larsen, B. et al. (Nov. 2001). "Less Pain on Injection by a New Formulation of Propofol?" *Der Anaesthesist.* 50(11):842-845.
Lilley, E.M.M. et al. (Sep. 1996). "The Effect of the Addition of Lignocaine on Propofol Emulsion Stability," *Anaesthesia* 51:815-818.

(56) References Cited

OTHER PUBLICATIONS

Mayer, M. et al. (1996). "Propofol und Etomidat-® Lipuro zur Einleitung einer Allgeneinanästhesie," *Der Anaesthesist* 45(11):1082-1084 and English translation of abstract only.

Meijs, W. E. et al. (May 1996). "A Facile Method for the Labeling of Proteins With Zirconium Isotopes," *Nuclear Medicine & Biology* 23(4):439-448.

Micha, J. P. et al. (Feb. 2006, e-pub Oct. 14 2005). "Abraxane in the Treatment of Ovarian Cancer: the Absence of Hypersensitivity Reactions," *Gynecol Oncol* 100(2):437-438.

Moreno-Aspitia, A. et al. (Oct. 2005). "North Central Cancer Treatment Group N0531: Phase II Trail of Weekly Albumin-bound Paclitaxel (ABI-007, Abraxane®) in Combination with Gemcitabine in Patients with Metastatic Breast Cancer," *Clinical Breast Cancer* 6(4):361-364.

Müller, B. G. et al. (Jan. 1996). "Albumin Nanospheres as Carriers for Passive Drug Targeting: An Optimized Manufacturing Technique," *Pharm. Res.* 13(1):32-37.

Nyman, D.W. et al. (Nov. 1, 2005). "Phase I and Pharmacokinetics Trial of ABI-007, a Novel Nanoparticle Formulation of Paclitaxel in Patients with Advanced Nonhematologic Malignancies," *J. Clin. Oncol.* 23(31):7785-7793.

O'Shaughnessy, J. et al. (2003). "ABI-007 (Abraxane$^{TM}$), A Nanoparticle Albumin-Bound (*nab*) Paclitaxel Demonstrates Superior Efficacy vs Taxol in MBC: A Phase III Trial," *Breast Cancer Res. Treat, Proceedings of the 26$^{th}$ Annual San Antonio Breast Cancer Symposium* (*SABCS*), San Antonio, Texas, Dec. 3-6, 2003, 82(Suppl. 1):3, Abstract No. 44, p. 182.

Paál, K. et al. (2001). "High Affinity Binding of Paclitaxel to Human Serum Albumin," *Eur. J. Biochem.* 268(7):2187-2191.

Paik, P. K. et al. (2011). "A Phase 2 Study of Weekly Albumin-Bound Paclitaxel (Abraxane®) Given As A Two-Hour Infusion," *Cancer. Chemother. Pharmacol.* 68(5):1331-1337.

Patelli, G. et al. (2002). "Effectiveness of Intraarterial Chemotherapy by Taxane Charged Albumine Nanoparticles on Advanced Squamous Cell Cancer of Oral Cavity and Oropharynx," *International Journal of Cancer* 18$^{th}$ UICC International Cancer Congress, Jun. 30-Jul. 5, 2002, Oslo, Norway, Abstract Book, Supplement 13, Abstract No. P 371, p. 258.

Purcell, M. et al. (2000). "Interaction of Taxol with Human Serum Albumin," *Biochim. Biophys. Acta* 1478:61-68.

Ritov, V. B. et al. (Jun. 2001). "Hexokinase Isozyme Distribution in Human Skeletal Muscle," *Diabetes* 50:1253-1262.

Rizvi, N. A. et al. (Feb. 1, 2008). "Phase I/II Trial of Weekly Intravenous 130-nm Albumin-Bound Paclitaxel as I1449tial Chemotherapy in Patients with Stage IV Non-Small-Cell Lung Cancer," *J. Clin. Oncol.* 26(4):639-643.

Rocha, J. L. L. et al. (Aug. 2002). "Uncommon Vancomycin-Induced Side Effects," *The Brazil. J. Infect. Diseases* 6(4):196-200.

Rugo, H. S. et al. (2012). "CALGB 40502/NCCTG N063H: Randomized phase III trial of weekly paclitaxel (P) compared to weekly nanoparticle albumin bound nab-paclitaxel (NP) or ixabepilone (Ix) with or without bevacizumab (B) as first-line therapy for locally recurrent or metastatic breast cancer (MBC)," abstract presented at the 2012 ASCO Annual Meeting, abstract located at http://www.asco.org/ASCOv2/Meetings/Abstracts?&vmview=abst_detail_view&confID=114&abstractID=99475, last visited on Aug. 14, 2012, Abstract No. CRA 1002, also published in *J. Clin. Oncol.* 30 (Suppl.), Abstract No. CRA 1002, 3 pages.

Shao, H. et al. (Jun. 2011). "Improved Response to *nab*-Paclitaxel Compared With Cremophor-Solubilized Paclitaxel is Independent of Secreted Protein Acidic and Rich in Cysteine Expression in Non-Small Cell Lung Cancer," *J. Thorac. Oncol.* 6(6):998-1005.

Shimoni, E. et al. (Jun. 1994). "Antioxidant Properties of Deferoxamine," *JAOCS* 71(6):641-644.

Singh, N. P. et al. (Nov. 21, 2001). "Selective Toxicity of Dihydroartemisinin and Holotransferrin Toward Human Breast Cancer Cells,"*Life Sci.* 70(1):49-56.

Socinski, M. A. et al. (2010). "Results of a Randomized, Phase III Trial of Nab-Paclitaxel (nab-P) and Carboplatin (C) Compared with Cremophor-Based Paclitaxel (P) and Carboplatin as First-Line Therapy in Advanced Non-Small Cell Lung Cancer (NSCLC)," Abstract for 2010 American Society of Cli1449cal Oncology Annual Meeting, Abstract Control No. 52889, located at http://www.asco.org/ASCOv2/Meetings/Abstracts?vmview=abst_detail_view&confID=74&abstractID=52889, last visited Oct. 10, 2010, *J. Clin. Oncol.* 28:18s (suppl. Abstr. LBA7511), 3 pages.

Sparreboom, A. et al. (Feb. 17, 1995). "Determination of Paclitaxel and Metabolites in Mouse Plasma, Tissues, Urine and Faeces by Semi-Automated Reversed-Phase High-Performance Liquid Chromatography," *J. Chromatogr. B. Biomed. Appl.* 664(2):383-391.

Sparreboom, A. et al. (Jun. 1, 2005). "Comparative Preclinical and Clinical Pharmacokinetics of a Cremophor-Free, Nanoparticle Albumin-Bound Paclitaxel (ABI-007) and Paclitaxel Formulated in Cremophor (Taxol)," *Clin. Cancer Res.* 11(11):4136-4143.

Sugio, S. et al. (1999). "Crystal Structure of Human Serum Albumin at 2.5 Å Resolution," *Protein Eng.* 12(6):439-446.

Tan, C.H. et al. (May 1998). "Pain on Injection of Propofol," *Anaesthesia* 53(5):468-476.

Taraboletti, G. et al. (2002, e-pub. Apr. 1, 2002). Antiangiogenic and Antitumor Activity of IDN 5390, a New Taxane Derivative, *Clin. Cancer Res.* 8:1182-1188.

Taylor, C. et al. (Dec. 2002). "Preliminary Evidence of Antitumor Activity of ABI-007, Cremophor-Free Nanoparticle Paclitaxel, in Patients Previoulsy Exposed to Taxanes," *Breast Cancer Research and Treatment*, 25$^{th}$ Annual San Antonio Breast Cancer Symposium (SABCS), San Antonio, Texas 76(Suppl. 1) Abstract No. 525, p. S132.

Tiruppathi, C. et al.(Jan. 1996). "Isolation and Characterization of a Cell Surface Albumin-Binding Protein From Vascular Endothelial Cells," *Proc. Natl. Acad. Sci. U.S.A.* 91:250-254.

Tonner, P.H. et al. (Nov. 1992). "The General Anesthetic Potency of Propofol and Its Dependence on Hydrostatic Pressure," *Anesthesiology* 77(5):926-931.

Tullis, J.L. (Jan. 24, 1977). "Albumin: 1. Background and Use," *JAMA* 237(4):355-360.

Tullis, J.L. (Jan. 31, 1977). "Albumin: 2. Guidelines for Clinical Use," *JAMA* 237(5):460-463.

Urien, S. et al. (May 1996). "Docetaxel Serum Protein Binding with High Affinity of Alpha$_1$-Acid Glycoprotein," *Invest. New Drugs* 14(2):147-151.

Vallejo, C. et al. (Dec. 1996). "Ifosfamide and Vinorelbine as First-Line Chemotherapy for Advanced Non-Small Cell Lung Carcinoma," *Am. J. Clin. Oncol.* 19(6):584-588.

Von Hoff, D. D. et al. (Dec. 1, 2011, e-pub: Oct. 3, 2011). "Gemcitabine Plus *nab*-Paclitaxel Is An Active Regimen In Patients With Advanced Pancreatic Cancer: A Phase I/II Trial," *J. Clin. Oncol.* 29(34):4548-4554.

Vorum, H. (Nov. 1999). "Reversible Ligand Binding to Human Serum Albumin," *Dan. Med. Bull.* 46(5):379-399.

Waugh, W.N. et al. (Jul. 1991). "Stability, Compatibility, and Plasticizer Extraction of Taxol (NSC-125973) Injection Diluted in Infusion Solutions and Stored in Various Containers," *AJHP* 48(7):1520-1524.

Yang, Y. Z. et al. (1993). "Alkylation of Human Albumin by the Antimalarial Artemisinin," *Biochem. Pharm.* 46(2):336-339.

Yang, A. et al. (Jul. 2003). "Pulmonary Delivery of a Novel, Cremophor-Free, Protein Based Nanoparticle Preparation of Paclitaxel," *Proceedings of the American Association of Cancer Research* (AACR) 94$^{th}$ Annual Meeting, Jul. 11-14, 2003, Washington Convention Center, Washington D.C. 44(2$^{nd}$ edition), Abstract No. 3672, p. 731.

International Search Report mailed Nov. 30, 2004, PCT Application No. PCT/US03/38941 filed Dec. 9, 2003, published as WO 2004/052401 on Jun. 24, 2004, eight pages.

European Search Report and European Search Opinion mailed on Jul. 22, 2011, for European Patent Application No. 111648143, filed on Dec. 9, 2003, six pages.

First Examination Report issued on Jan. 7, 2008, by Indian Patent Office ("Controller of Patents") for Indian Patent Application No. 2899/DELNP/2005, owned by Applicant American BioScience, Inc. (now "Abraxis BioScience LLC"), 12 pages.

(56) References Cited

OTHER PUBLICATIONS

Response to First Examination Report filed on Jan. 6, 2009, with the Indian Patent Office, by Applicant for Indian Patent Application No. 2899/DELNP/2005, 15 pages.
Pre-grant opposition on Sep. 4, 2008, submitted by Opponent ("Natco Pharma Ltd.") against Indian Patent Application No. 2899/DELNP/2005, 149 pages.
Reply filed by Applicant on Jan. 9, 2009, to the pre-grant opposition filed by Opponent against Indian Patent Application No. 2899/DELNP/2005, 30 pages total.
Additional Submission from Opponent dated Mar. 10, 2009, to the Indian Patent Office in response to the reply filed by Applicant, 179 pages.
Submission from Applicant dated Apr. 8, 2009 to Indian Patent Office, pertaining to the prosecution of Indian Patent Application No. 2899/DELNP/2005, 134 pages.
Submission filed by Applicant on May 4, 2009, pertaining to arguments made during the oral hearing of the pre-grant opposition of Indian Patent Application No. 2899/DELNP/2005, held on Apr. 9, 2009, before the Controller of Patents, 22 pages.
Decision of the Indian Controller of Patents dated Jul. 24, 2009, with respect to the pre-grant opposition filed against Indian Patent Application No. 2899/DELNP/2005, 33 pages.
Civil Writ Petition filed Applicant/Petitioner ("Abraxis BioScience, LLC") with the High Court of Delhi at New Delhi, India, on Nov. 26, 2009, challenging the decision of the Indian Controller of Patents dated Jul. 24, 2009, to refuse the grant of Indian Patent Application No. 2899/DELNP/2005/300, 29 pages total.
Appeal filed by Applicant/Appellant ("Abraxis BioScience, LLC") with the Intellectual Property Appeal Board on Nov. 27, 2009, against the decision of the Indian Controller of Patents dated Jul. 24, 2009, refusing to grant Indian Patent Application No. 2899/DENLP/2005, 71 pages.
Notice from Intellectual Property Appellate Board to Opponent/Respondent No. 4 ("Natco Pharma Ltd.") dated Jan. 11, 2010, of the filing of an Appeal by Applicant/Appellant under Appeal No. OA/3/2010/PT/DEL/302, against the decision of the Indian Controller of Patents and Designs dated Jul. 24, 2009, (Form 'C'), one page.
Counter statement and reply to miscellaneous petition for appointing early hearing filed by Respondent No. 4 on May 8, 2010, with the Intellectual Property Appellate Board, with respect to Appeal No. OA/3/2010/PT/DEL, 112 pages.
Reply filed by Applicant/Appellant on Aug. 7, 2010, with the Intellectual Property Appellate Board, 120 pages.
U.S. Appl. No. 12/479,710, filed Jun. 5, 2009, for Desai et al.
U.S. Appl. No. 13/776,481, filed Feb. 25, 2013, for Desai et al.
U.S. Appl. No. 13/776,484, filed Feb. 25, 2013, for Desai et al.
U.S. Appl. No. 13/777,980, filed Feb. 26, 2013, for Desai et al.
U.S. Appl. No. 13/777,988, filed Feb. 26, 2013, for Desai et al.
U.S. Appl. No. 13/779,625, filed Feb. 27, 2013, for Desai et al.
U.S. Appl. No. 13/779,624, filed Feb. 27, 2013, for Desai et al.
U.S. Appl. No. 13/779,621, filed Feb. 27, 2013, for Desai et al.
U.S. Appl. No. 13/781,482, filed Feb. 28, 2013 for Desai et al.
U.S. Appl. No. 13/781,479, filed Feb. 28, 2013, for Desai et al.
U.S. Appl. No. 13/781,489, filed Feb. 28, 2013, for Trieu et al.
U.S. Appl. No. 13/781,480, filed Feb. 28, 2013, for Yeo et al.
U.S. Appl. No. 13/782,990, filed Mar. 1, 2013, for Desai et al.
U.S. Appl. No. 13/782,988, filed Mar. 1, 2013, for Desai et al.
U.S. Appl. No. 13/782,984, filed Mar. 1, 2013, for Desai et al.
U.S. Appl. No. 13/783,122, filed Mar. 1, 2013, for Desai et al.
U.S. Appl. No. 13/701,001, internationally filed on May 20, 2011, for Desai et al.
U.S. Appl. No. 13/782,992, filed Mar. 1, 2013, for Desai et al.
U.S. Appl. No. 13/794,705, filed Mar. 12, 2013, for Desai et al.
U.S. Appl. No. 13/791,841, filed Mar. 12, 2013, for Desai et al.
U.S. Appl. No. 13/794,480, filed Mar. 12, 2013, for Desai et al.
U.S. Appl. No. 13/794,486, filed Mar. 12, 2013, for Heise et al.
U.S. Appl. No. 13/794,712, filed Mar. 11, 2013, for Pierce et al.
Anonymous. (Mar. 24, 2003). "Coated Stents for Prevention of Coronary Arteries Restenosis," *China Academic Journal Electronic Publishing House* pp. 49-53. (Translation of the Abstract Only.).

COMPOSITIONS AND METHODS OF DELIVERY OF PHARMACOLOGICAL AGENTS

CROSS-REFERENCE TO RELATED PATENT APPLICATIONS

This patent application is a continuation of patent application Ser. No. 13/038,287, filed Mar. 1, 2011; which is a continuation of patent application Ser. No. 12/758,413, filed Apr. 12, 2010, now U.S. Pat. No. 7,923,536; which is a continuation of patent application Ser. No. 11/553,339, filed Oct. 26, 2006, now U.S. Pat. No. 7,820,788; which is a continuation of patent application Ser. No. 10/731,224, filed Dec. 9, 2003, now abandoned; which claims the benefit of U.S. Provisional Patent Application Ser. No. 60/432,317, filed Dec. 9, 2002; U.S. Provisional Patent Application Ser. No. 60/526,544, filed Dec. 3, 2003; U.S. Provisional Patent Application Ser. No. 60/526,773, filed Dec. 4, 2003; and U.S. Provisional Patent Application Ser. No. 60/527,177, filed Dec. 5, 2003, the content of each of which is hereby incorporated by reference in their entirety.

FIELD OF THE INVENTION

This invention pertains to pharmaceutical-compositions comprising pharmaceutically active agents for parenteral or other internal use, which have the effect of reducing certain undesirable side effects upon administration when compared with available formulations of similar drugs.

BACKGROUND OF THE INVENTION

It is well recognized that many drugs for parenteral use, especially those administered intravenously, cause undesirable side effects such as venous irritation, phlebitis, burning and pain on injection, venous thrombosis, extravasation, and other administration related side effects. Many of these drugs are insoluble in water, and are thus formulated with solubilizing agents, surfactants, solvents, and/or emulsifiers that are irritating, allergenic, or toxic when administered to patients (see, e.g., Briggs et al., *Anesthesis* 37, 1099 (1982), and Waugh et al., *Am. J. Hosp. Pharmacists*, 48, 1520 (1991)). Often, the free drug present in the formulation induces pain or irritation upon administration. For example, phlebitis was observed in 50% of patients who received peripheral vein administration of ifosfamide and vinorelbine as first-line chemotherapy for advanced non-small cell lung carcinoma. (see, e.g., Vallejo et al., *Am. J. Clin. Oncol.*, 19(6), 584-8 (1996)). Moreover, vancomycin has been shown to induce side effects such as phlebitis (see, e.g., Lopes Rocha et al., *Braz. J. Infect. Dis.*, 6(4), 196-200 (2002)). The use of cisplatin, gemcitabine, and SU5416 in patients with solid tumors has resulted in adverse events such as deep venous thromboses and phlebitis (see, e.g., Kuenen et al., *J. Clin. Oncol.*, 20(6), 1657-67 (2002)). In addition, propofol, an anesthetic agent, can induce pain on injection, burning and vein irritation, particularly when administered as a lecithin-stabilized fat emulsion (see, e.g, Tan et al., *Anathesia*, 53, 468-76, (1998)). Other drugs that exhibit administration-associated side effects include, for example, Taxol (paclitaxel) (see, e.g., package insert for Taxol I.V.), codarone (amiodarone hydrochloride) (see, e.g., package insert for Codarone I.V.), the thyroid hormone T3 or liothyronine (commercially available as Triostat), thiotepa, bleomycin, and diagnostic radiocontrast agents.

Another problem associated with the manufacture of drugs for injection, particularly water insoluble drugs, is the assurance osterility. Sterile manufacturing of drug emulsions/dispersions can be accomplished by absolute sterilization of all the components before manufacture, followed by absolutely aseptic technique in all stages of manufacture. However, such methods are time consuming and expensive. In addition, the oxidation of drug formulations by exposure to air during manufacture or storage can lead to, for example, reduced pH, drug degradation, and discoloration, thereby destabilizing the drug formulation and/or reducing shelf life.

To circumvent the problems associated with administration-related side effects of drug formulations, alternate formulations have been attempted. With respect to propofol, for example, methods for reducing propofol-induced pain include increasing the fat content of the solvent (e.g., long chain triglycerides (LCT)), premedication, pretreatment with non-steroidal drugs, local anaesthetics, opioids, the addition of lidocaine, the addition of cyclodextrin, and microfiltration (see, e.g., Mayer et al., *Anaesthesist*, 45(11), 1082-4 (1996), Davies, et al. *Anaesthesia*, 57, 557-61 (2002), Doenicke, et al., *Anaesth. Analg*, 82, 472-4 (1996), Larsen et al., *Anaesthesitis* 50, 842-5 (2001), Lilley et al., *Anaesthesia*, 51, 815-8 (1996), Bielen et al., *Anesth. Analg.*, 82(5), 920-4 (1996), and Knibbe et al., *Br. J. Clin. Pharmacol.*, 47(6), 653-60. (1999)). These formulations, however, induce other side effects (e.g., cardiovascular complications), or cause destabilization of propofol emulsions.

To overcome the problem of bacterial contamination, propofol formulations have been developed with antibacterial agents, such as an EDTA equivalent (e.g., edetate), pentetate, or sulfite-containing agents, or they have been have been formulated with a lower pH (see, e.g., U.S. Pat. Nos. 5,714,520, 5,731,355, 5,731,356, 6,028,108, 6,100,302, 6,147,122, 6,177,477, 6,399,087, 6,469,069, and International Patent Application No. WO 99/39696). Since edetate and pentetate are metal ion chelators, however, they have the potential to be dangerous by scavenging the essential metal ions from the body system. Moreover, the addition of sulphites to drug formulations presents potential adverse effects to the pediatric population and for those in the general population who are allergic to sulphur.

Thus, there remains a need for a composition and method that reduce or eliminate the side effects associated with the parenteral or in vivo administration of drugs, There also is a need for a pharmaceutical composition that is sterile, and methods of preparing such a composition. In addition, there is a need for a pharmaceutical composition and method that reduce or eliminate oxidation of pharmaceutical formulations to prevent drug destabilization.

The invention provides such compositions and methods. These and other advantages of the invention, as well as additional inventive features, will be apparent from the description of the invention provided herein.

BRIEF SUMMARY OF THE INVENTION

The invention provides various embodiments of pharmaceutical compositions. One, some, or all of the properties of the various embodiments can be found in different embodiments of the invention and still fall within the scope of the appended claims.

The invention provides a pharmaceutical composition comprising a pharmaceutical agent and a pharmaceutically acceptable carrier, wherein the pharmaceutically acceptable carrier comprises a protein, such as albumin, more preferably human serum albumin, in an amount effective to reduce one or more side effects of administration of the pharmaceutical composition into a human, and wherein the pharmaceutically acceptable carrier comprises deferoxamine in an amount effective to inhibit microbial growth in the pharmaceutical composition. The invention also provides a pharmaceutical composition comprising a pharmaceutical agent and a pharmaceutically acceptable carrier, wherein the pharmaceutically acceptable carrier comprises a protein, such as albumin, in an amount effective to reduce one or More side effects of administration of the pharmaceutical composition into a human, and wherein the pharmaceutically acceptable carrier comprises deferoxamine in an amount effective to inhibit oxidation in the pharmaceutical composition.

The invention provides a method for reducing one or more side effects associated with Administration of a pharmaceutical composition to a human comprising (a) administering to a human a pharmaceutical composition comprising a pharmaceutical agent and a pharmaceutically acceptable carrier, wherein the pharmaceutically acceptable carrier comprises albumin and deferoxamine. Also provided are methods for inhibiting microbial growth, or for inhibiting oxidation, or for inhibiting microbial growth and oxidation in a pharmaceutical composition. These methods comprise preparing a pharmaceutical composition comprising a pharmaceutical agent and a pharmaceutically acceptable carrier, wherein the pharmaceutically acceptable carrier comprises deferoxamine in an amount effective for inhibiting microbial growth or in an amount effective for inhibiting oxidation in the pharmaceutical composition.

The invention also provides a method for enhancing transport of a pharmaceutical agent to the site of an infirmity, which method comprises administering to a human a pharmaceutical composition comprising a pharmaceutical agent and a pharmaceutically acceptable carrier, wherein the pharmaceutically acceptable carrier comprises albumin, and wherein the ratio of albumin to pharmaceutical agent in the pharmaceutical composition is about 18:1 or less. The invention further provides a method for enhancing binding of a pharmaceutical agent to a cell in vitro or in vivo, which method comprises administering to said cell in vitro or in vivo a pharmaceutical composition comprising a pharmaceutical agent and a pharmaceutically acceptable carrier, wherein the pharmaceutically acceptable carrier comprises albumin, and wherein the ratio of albumin to pharmaceutical agent in the pharmaceutical composition is about 18:1 or less.

The invention also provides a pharmaceutical composition comprising a pharmaceutical agent and a pharmaceutically acceptable carrier, wherein the pharmaceutically acceptable carrier comprises albumin in an amount effective to increase transport of the drug to the site of infirmity in a human, and wherein the ratio of albumin to pharmaceutical agent is about 18:1 or less.

The invention further provides a method for increasing the transport of a pharmaceutical agent to a cell in vitro or in vivo by combining said agent with a protein, wherein said protein binds a specific cell-surface receptor on said cell, wherein said binding of the protein-pharmaceutical agent combination with the said receptor causes the transport to occur, and wherein the ratio of protein to pharmaceutical agent is about 18:1 or less.

DETAILED DESCRIPTION OF THE INVENTION

The invention provides a pharmaceutical composition comprising a pharmaceutical agent and a pharmaceutically acceptable carrier, wherein the pharmaceutically acceptable carrier comprises a protein such as albumin, preferably human serum albumin, in an amount effective to reduce one or more side effects of administration of the pharmaceutical composition to a human, and wherein the pharmaceutically acceptable carrier comprises deferoxamine in an amount effective to inhibit microbial growth in the pharmaceutical composition. The invention also provides a pharmaceutical composition comprising a pharmaceutical agent and a pharmaceutically acceptable carrier, wherein the pharmaceutically acceptable carrier comprises a protein such as albumin in an amount effective to reduce one or more side effects of administration of the pharmaceutical composition to a human, and wherein the pharmaceutically acceptable carrier comprises deferoxamine in an amount effective to inhibit oxidation in the pharmaceutical composition.

Any suitable pharmaceutical agent can be used in the inventive pharmaceutical composition. Suitable pharmaceutical agents include, but are not limited to, anticancer agents or antineoplastics, antimicrotubule agents, immunosuppressive agents, anesthetics, hormones, agents for use in cardiovascular disorders, antiarrythmics, antibiotics, antifungals, antihypertensives, antiasthmatics, analgesics, anti-inflammatory agents, anti-arthritic agents, and vasoactive agents. The invention is useful with many other drug classes as well. More specifically, suitable pharmaceutical agents include, but are not limited to, taxanes, (e.g., Taxol® (paclitaxel), and Taxotere™ (docetaxel)), epothilones, camptothecin, colchicine, amiodarone, thyroid hormones, vasoactive peptides (e.g., vasoactive intestinal peptide), amphotericin, corticosteroids, propofol, melatonin, cyclosporine, rapamycin (sirolimus), tacrolimus, mycophenolic acids, ifosfamide, vinorelbine, vancomycin, gemcitabine, SU5416, thiotepa, bleomycin, diagnostic radiocontrast agents, and derivatives thereof. Other drugs that are useful in the inventive composition are described in, for example, U.S. Pat. No. 5,916,596 and co-pending U.S. patent application Ser. No. 09/446,783. Preferably, the pharmaceutical agent is propofol, paclitaxel, or docetaxel. More preferably, the pharmaceutical agent is propofol or paclitaxel. Most preferably, the pharmaceutical agent is propofol.

Taxol® (paclitaxel) (Bristol-Myers Squibb) is active against carcinomas of the ovary, breast, lung, esophagus and head and neck. Taxol, however, has been shown to induce toxicities associated with administration, as well significant acute and cumulative toxicity, such as myelosuppression, neutropenic fever, anaphylactic reaction, and peripheral neuropathy. Because paclitaxel is poorly soluble in water, cremophor typically is used as a solvent, requiring large infusion volumes and special tubing and filters. Cremophor is associated with side effects that can be severe, including anaphylaxis and other hypersensitivity reactions that can require pretreatment with corticosteroids, antihistamines, and $H_2$ blockers (see, e.g., Gelderblom et al., *Eur. J. of Cancer*, 37, 1590-1598, (2001)). Taxotere™ (docetaxel) is used in treatment of anthracycline-resistant breast cancer, but also has previously been shown to induce side effects of hypersensitivity and fluid retention that can be severe. Epothilone (and derivatives thereof) also typically is administered in cremophor, and has been shown to induce severe neutropenia, hypersensitivity, and neuropathy.

Propofol (2,6-diisopropylphenol) is a hydrophobic, water-insoluble oil, which is widely used as an intravenous anesthetic agent to induce and maintain general anesthesia and sedation of humans and animals. Propofol typically is administered directly into the bloodstream and crosses the blood-brain barrier. Pharmaceutical compositions comprising propofol must have sufficient lipid solubility to cross this bather and depress the relevant mechanisms of the brain. Propofol has a maximum solubility in water of 1.0+/−0.02 μM at 22.5° C. (see, e.g., Tonner et al., *Anesthesiology*, 77, 926-931

(1992)). As such, propofol is generally formulated as an emulsion containing solubilizing agents, surfactants, solvents, or as an oil-in-water emulsion (see, e.g., U.S. Pat. Nos. 6,150,423, 6,326, 406, and 6,362,234). In addition to the active pharmaceutical agent, the compositions of the present invention include pharmaceutical carriers, or excipients. The choice of carrier is not necessarily critical, and any of the carriers known in the art can be used in the composition. The choice of carrier is preferably determined, in part, by the particular site to which the pharmaceutical composition is to be administered and the particular method used to administer the pharmaceutical composition. Preferably, the pharmaceutically acceptable carrier comprises proteins. Any suitable protein can be used. Examples of suitable proteins include, but are not limited to albumin, immunoglobulins including IgA, lipoproteins, apolipoprotein B, beta-2-macroglobulin, thyroglobulin and the like. Most preferably, the pharmaceutically acceptable carrier comprises albumin, most preferably human serum albumin. Proteins, including albumin, suitable for the invention may be natural in origin or synthetically prepared.

Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see; e.g., Finlayson; *Seminars in Thrombosis and Hemostasis*, 6, 85-120, (1980)).

Human serum albumin (HSA) has multiple hydrophobic binding sites (a total of eight for fatty acids, an endogenous ligand of HSA) and binds a diverse set of drugs, especially neutral and negatively charged hydrophobic compounds (Goodmanet at, *The Pharmacological Basis of Therapeutics*, $9^{th}$ ed, McGraw-Hill N.Y. (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol*, 30, 687-92 (1981), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998); Sugio et al., *Protein. Eng.*, 12, 439-46 (1999), He et al., Nature, 358, 209-15 (1992), and Carter et al.; *Adv. Protein. Chem.*, 45, 153-203 (1994)). Paclitaxel and propofol have been shown to bind HSA (see; e.g., Paal et al., *Eur. J. Biochem.*, 268(7), 2187-91 (2001), Purcell et al., *Biochem. Biophys. Acta*, 1478(1), 61-8 (2000), Altmayer et at, *Arzneimittelforschung*, 45, 1053-6 (1995), and Gamido et al. *Rev. Esp. Anestestiol. Reanim.*, 41, 308-12 (1994)). In addition, docetaxel has been shown to bind to human plasma proteins (see, e.g., Urien et al., *Invest. New. Drugs*, 14(2), 147-51 (1996)). Thus, while not wishing to be bound to any particular theory, it is believed that the inclusion of pro pins such as albumin in the inventive pharmaceutical compositions results in a reduction in side effects associated with administration of the pharmaceutical composition that is due, at least in part, to the binding of human serum albumin to any free drug that is present in the composition.

The amount of albumin included in the pharmaceutical composition of the present invention will vary depending on the pharmaceutical active agent, other excipients, and the route and site of intended administration. Desirably, the amount of albumin included in the composition is an amount effective to reduce one or more side effects the active pharmaceutical agent due to the of administration of the inventive pharmaceutical composition to a human. Typically, the pharmaceutical composition is prepared in liquid form, and the albumin is then added in solution. Preferably, the pharmaceutical composition, in liquid form, comprises from about 0.1% to about 25% by weight (e.g. about 0.5% by weight, about 5% by weight, about 10% by weight, about 15% by weight, or about 20% by weight) of albumin. Most preferably, the pharmaceutical composition, in liquid form, comprises about 0.5% to about 5% by weight of albumin. The pharmaceutical composition can be dehydrated, for example, by lyophilization, spray-drying, fluidized-bed drying, wet granulation, and other suitable methods known in the art. When the composition is prepared in solid form, such as by wet granulation, fluidized-bed drying, and other methods known to those skilled in the art, the albumin preferably is applied to the active pharmaceutical agent, and other excipients if present, as a solution. The HSA solution preferably is from about 0.1% to about 25% by weight (about 0.5% by weight, about 5% by weight, about 10% by weight, about 15% by weight, or about 20% by weight) of albumin.

In addition to albumin, the compositions of the present invention preferably comprise deferoxamine. Deferoxamine is a natural product isolated from *Streptomyces pilosus*, and is capable of forming iron complexes. Deferoxamine mesylate for injection USP, for example, is approved by the Food and Drug Administration as an iron-chelating agent and is available for intramuscular, subcutaneous, and intravenous administration. Deferoxamine mesylate USP is a white to off-white powder. It is freely soluble in water and its molecular weight is 656.79. The chemical name for deferoxamine mesylate is N-[5-[3-[(5-aminopentyl)-hydroxycarbamoyl]-propionamido]pentyl]-3[[5-((N-hydroxyacetamido)pentyl]-carbamoyl]propionohydroxamic acid monomethanesulfonate (salt), and its structural formula is $C_{25}H_{48}N_6O_8 \cdot CH_3SO_3H$. As described in the Examples, deferoxamine, or analogs, derivatives, or salts (e.g., mesylate salts) thereof inhibits microbial growth and oxidation in the pharmaceutical composition, and it is believed to bind to free drug in the composition. Deferoxamine also has been shown to bind to phenolic compounds (see, e.g., Juven et al., *J. Appl. Bacteriol.*, 76(6), 626-31 (1994)). Paclitaxel, docetaxel, propofol, and the like, are either phenolic like or have phenolic or phenyl substituents. Therefore, it is believed that deferoxamine can bind to or reduce the amount of free drug in the inventive pharmaceutical composition, thereby also reducing or alleviating irritation or pain upon injection.

The amount of deferoxamine, or its preferred salt, i.e., a mesylate salt of deferoxamine, included in the composition will depend on the active pharmaceutical agent and other excipients. Desirably, the amount of deferoxamine, its salts, and analogs thereof in the composition is an amount effective to inhibit microbial growth and/or inhibit oxidation. As described above, typically the pharmaceutical composition is prepared in liquid form, and deferoxamine, it salts, and analogs thereof, is then added in solution. Preferably, the pharmaceutical composition, in liquid form, comprises from about 0.0001% to about 0.5% by weight (e.g., about 0.005% by weight, about 0.1%, or about 0.25% by weight) of deferoxamine, its salts, or its analogs. More preferably, the composition, in liquid form, comprises like amounts of the preferred deferoxamine salt, deferoxamine mesylate. Most preferably, the pharmaceutical composition, in liquid form, comprises about 0.1% by weight of deferoxamine mesylate. When the composition is prepared in solid form, as described above, such as by wet granulation, fluidized-bed drying, and other methods known to those skilled in the art, deferoxamine mesylate preferably is applied to the active pharmaceutical agent, and other excipients if present, as a solution. The deferoxamine mesylate solution preferably is from about 0.0001% to about 0.5% by weight (e.g., about 0.005% by weight, about 0.1%, or about 0.25% by weight) of deferoxamine.

In keeping with the invention, the pharmaceutical composition can include other agents, excipients, or stabilizers to improve properties of the composition. For example, to increase stability by increasing the negative zeta potential of nanoparticles or nanodroplets, certain negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including Lecithin (Egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), D-α-phosphatidylcholine, β-acetyl-γ-O-hexadecyl, L-α-phosphatidylcholine, β-acetyl-γ-O-hexadecyl, DL-α-phosphatidylcholine, β-acetyl-γ-O-hexadecyl, L-α-phosphatidylcholine, β-acetyl-γ-O-Octadecyl, L-α-phosphatidylcholine, β-arachidonoyl-γ-O-hexadecyl, L-α-phosphatidylcholine, β-acetyl-γ-O-(octadec-9-cis-enyl), D-α-phosphatidylcholine, β-arachidonoyl-γ-O-palmitoyl, 3-sn-phosphatidylcholine, 2-arachidinoyl-1-stearoyl, L-α-phosphatidylcholine, β-arachidonoyl-γ-stearoyl, L-α-phosphatidylcholine, diarachidoyl, L-α-phosphatidylcholine, dibehenoyl, L-α-phosphatidylcholine, β-(cis-8,11,14-eicosatrienoyl)-γ-O-hexadecyl, L-α-phosphatidylcholine, β-oleoyl-γ-myristoyl, L-α-phosphatidylcholine, β-(pyren-1-yl) decanoyl-γ-palmitoyl, 3-sn-phosphatidyl-N,N-dimethylethanolamine, 1,2-dipalmitoyl, L-α-phosphatidylethanolamine, diheptadecanoyl, 3-sn-phosphatidylethanolamine, 1,2-dilauroyl, 3-sn-phosphatidylethanolamine, 1,2-dimyristoyl, 3-sn-phosphatidylethanolamine, 1,2-dioleoyl, 3-sn-phosphatidylethanolamine, 1,2-dipalmitoyl, L-α-phosphatidylethanolamine, dipalmitoyl, L-α-phosphatidylethanolamine, dipalmitoyl, N-dansyl, L-α-phosphatidylethanolamine, dipalmitoyl, N,N-dimethyl, L-α-dimyristoylphosphatidylglycerol (sodium salt) (DMPG), dipalmitoylphosphatidylglycerol (sodium salt) (DPPG), distearoylphosphatidylglycerol (sodium salt) (DSPG), N-(carbonyl-methoxypolyethylene glycol 2000)-1,2-distearoyl-sn-glycero-3-phosphoethanolamine sodium (MPEG-DSPE), L-α-phosphatidic acid, didecanoyl sodium salt, L-α-phosphatidic acid, diheptadecanoyl sodium salt, 3-sn-phosphatidic acid, 1,2-dimyristoyl sodium salt, L-α-phosphatidic acid, dioctanoyl sodium salt, L-α-phosphatidic acid, dioleoyl sodium salt, L-α-phosphatidic acid, dipalmitoyl sodium salt, L-α-Phosphatidyl-DL-glycerol, dimyristoyl sodium salt, L-α-phosphatidyl-DL-glycerol, dioleoyl sodium salt, L-α-phosphatidyl-DL-glycerol, dipalmitoyl ammonium salt, L-α-phosphatidyl-DL-glycerol, distearoyl ammonium salt, L-α-phosphatidyl-DL-glycerol, p-oleoyl-γ-palmitoyl ammonium salt, L-α-phosphatidylinositol ammonium salt, L-α-phosphatidylinositol sodium salt, L-α-phosphatidyl-L-serine, dioleoyl sodium salt, L-α-phosphatidyl-L-serine, and dipalmitoyl sodium salt. Negatively charged surfactants of emulsifiers are also suitable as additives, e.g., sodium cholesteryl sulfate and the like.

The pharmaceutical agent (e.g., propofol) may be used alone or dissolved in a water-immiscible solvent. A wide range of water-immiscible solvents such as soybean, safflower, cottonseed, corn, sunflower, arachis, castor, or olive oil may be used. The preferred oil is a vegetable oil, wherein soybean oil is most preferred. Soybean oil may be used in a range of 1% to 10% by weight of the composition. Preferably soybean oil is present in the pharmaceutical composition in an amount of about 3% by weight.

The inventive pharmaceutical composition can be stabilized with a pharmaceutically acceptable surfactant. The term "surfactants," as used herein, refers to surface active group(s) of amphiphile molecules. Surfactants can be anionic, cationic, nonionic, and zwitterionic. Any suitable surfactant can be included in the inventive pharmaceutical composition. Suitable surfactants include non-ionic surfactants such as phosphatides, polyoxyethylene sorbitan esters, and tocopheryl polyethylene glycol succinate. Preferable surfactants are egg lecithin, tween 80, and vitamin E-t d-α-tocopheryl polyethylene glycol-1000 succinate (TPGS). For soybean oil containing formulations, egg lecithin is preferred and is no more than 1.2% by weight for a formulation containing 3% soybean oil, preferably at 1.1% by weight of the composition. For formulations without soybean oil, tween 80 or vitamin E-TPGS are the preferred surfactants. Typically, 0.1 to 1.5% by weight of tween 80 or 0.5 to 4% by weight of vitamin E-TPGS is suitable. Preferably, 1.5% by weight of tween 80 or 1% by weight of vitamin E-TPGS is used. Examples of other suitable surfactants are described in, for example, Becher, *Emulsions: Theory and Practice*, Robert E. Krieger Publishing, Malabar, Fla. (1965).

There are a wide variety of suitable formulations of the inventive pharmaceutical composition (see, e.g., U.S. Pat. No. 5,916,596). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium; talc, magnesium stearate, stearic acid, and other excipients, colorants, diluents, buffering agents, moistening agents, preservatives, flavoring agents; and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents; stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

Formulations suitable for aerosol administration comprise the inventive pharmaceutical composition include aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizers, and preservatives, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Other suitable formulations are possible, for example, suppositories can be prepared by use of a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

In a preferred embodiment of the invention, the pharmaceutical composition is formulated to have a pH range of 4.5 to 9.0, and more preferably a pH of 5.0 to 8.0. The pharmaceutical composition can also be made to be isotonic with blood by the addition of a suitable tonicity modifier, such as glycerol. Moreover, the pharmaceutically acceptable carrier preferably also comprises pyrogen-free water or water for injection, USP. Preferably, the inventive pharmaceutical composition is prepared as a sterile aqueous formulation, a nanoparticle, an oil-in-water emulsion, or a water-in-oil emulsion. Most preferably, the pharmaceutical composition is an oil-in-water emulsion.

For a pharmaceutical composition comprising propofol, in accordance with the invention, an oil-in-water emulsion is prepared by dissolving propofol in a water-immiscible solvent alone, and preparing an aqueous phase containing albumin, deferoxamine, a surfactant, and other water-soluble ingredients, and mixing the oil with the aqueous phase. The crude emulsion is high pressure homogenized at pressures of 10,000 to 25,000 psi and recirculated for 5 to 20 cycles to form an ideal emulsion. The preferred pressure is 15,000 to 20,000 psi., and more preferably 10,000 psi. The crude emulsion may be recirculated from 7 to 15 cycles and is preferably recirculated at 15 cycles. Alternatively, discrete passes through a homogenizer may be used.

Preferably, the inventive pharmaceutical composition can have a particle or droplet size less than about 200 nanometers (nm). For example, in the case of paclitaxel, docetaxel, rapamycin, cyclosporine, propofol and others, the mean size of these dispersions is less than 200 nm.

The invention further provides a method for reducing one or more side effects associated with administration of a pharmaceutical composition to a human. The method comprises administering to a human a pharmaceutical composition comprising a pharmaceutical agent and a pharmaceutically acceptable carrier, wherein the pharmaceutically acceptable carrier comprises albumin and deferoxamine. Descriptions of the pharmaceutical composition, pharmaceutical agent, and pharmaceutically acceptable carrier, and components thereof set forth above in connection with the inventive pharmaceutical composition, also are applicable to those same aspects of the inventive method.

The dose of the inventive pharmaceutical composition administered to a human, in the context of the invention, will vary with the particular pharmaceutical composition, the method of administration, and the particular site being treated. The dose should be sufficient to effect a desirable response, such as a therapeutic or prophylactic response against a particular disease, or, when the pharmaceutical agent is an anaesthesia, such as propofol, an anesthetic response, within a desirable time frame.

While any suitable means of administering the pharmaceutical composition to the human can be used within the context of the invention, preferably the inventive pharmaceutical composition is administered to the human via intravenous administration, intra-arterial administration, intrapulmonary administration, oral administration, inhalation, intravesicular administration, intramuscular administration, intra-tracheal administration, subcutaneous administration, intraocular administration, intrathecal administration, or transdermal administration. For example, the inventive pharmaceutical composition can be administered by inhalation to treat conditions of the respiratory tract. There are minimal side-effects associated with the inhalation of the inventive pharmaceutical composition, as albumin is a natural component in the lining and secretions of the respiratory tract. The inventive composition can be used to treat respiratory conditions such as pulmonary fibrosis, broncheolitis obliterans, lung cancer, bronchoalveolar carcinoma, and the like.

The inventive method results in the reduction of one or more side effects associated with administration of a pharmaceutical composition to a human. Such side effects include, for example, myelosuppression, neurotoxicity, hypersensitivity, inflammation, venous irritation, phlebitis, pain, skin irritation, and combinations thereof. These side effects, however, are merely exemplary, and other side effects, or combination of side effects, associated with various pharmaceutical agents can be reduced or avoided by the use of the novel compositions and methods of the present invention.

The invention further provides a method for inhibiting microbial growth in a pharmaceutical composition. By "inhibiting microbial growth" is meant either a complete elimination of microbes from the pharmaceutical composition, or a reduction in the amount or rate of microbial growth in the pharmaceutical composition. The method comprises preparing a pharmaceutical composition comprising a pharmaceutical agent and a pharmaceutically acceptable carrier, wherein the pharmaceutically acceptable carrier comprises deferoxamine, its salts, its analogs, and combinations thereof, in an amount effective for inhibiting microbial growth in the pharmaceutical composition. In addition, the invention provides a method for inhibiting oxidation of a pharmaceutical composition. This method comprises preparing a pharmaceutical composition comprising a pharmaceutical agent and a pharmaceutically acceptable carrier, wherein the pharmaceutically acceptable carrier comprises deferoxamine, its salts, its analogs, and combinations thereof, in an amount effective for inhibiting oxidation of the pharmaceutical composition. Descriptions of the pharmaceutical composition, pharmaceutical agent, and pharmaceutically acceptable carrier, and components thereof set forth above in connection with the inventive pharmaceutical composition, also are applicable to those same aspects of the inventive method.

The amount of deferoxamine, or its preferred salt, a mesylate salt of deferoxamine, included in the composition will depend on the active pharmaceutical agent and other excipients. Desirably, the amount of deferoxamine, its salts, and analogs thereof in the composition is an amount effective to inhibit microbial growth and/or inhibit oxidation. As described above, typically, the pharmaceutical composition is prepared in liquid form, and deferoxamine, it salts, and analogs thereof, is then added in solution. Preferably, the pharmaceutical composition, in liquid form, comprises from about 0.0001% to about 0.5% by weight (e.g., about 0.005% by weight, about 0.1%, or about 0.25% by weight) of deferoxamine, its salts, or its analogs. More preferably, the composition, in liquid form, comprises like amounts of the preferred deferoxamine salt, deferoxamine mesylate. Most preferably, the pharmaceutical composition, in liquid form, comprises about 0.5% by weight of deferoxamine mesylate. When the composition is prepared in solid form, as described above, such as by wet granulation, fluidized-bed drying, and other methods known to those skilled in the art, deferoxamine mesylate preferably is applied to the active pharmaceutical agent, and other excipients if present, as a solution. The deferoxamine mesylate solution preferably is from about 0.0001% to about 0.5% by weight (e.g., about 0.005% by weight, about 0.1%, or about 0.25% by weight) of deferoxamine.

The invention also provides a method for enhancing transport of a pharmaceutical agent to the site of an infirmity, which method comprises administering to a human a pharmaceutical composition comprising a pharmaceutical agent and a pharmaceutically acceptable carrier, wherein the pharmaceutically acceptable carrier comprises albumin, and wherein the ratio of albumin to pharmaceutical agent in the pharmaceutical composition is about 18:1 or less. The invention further provides a method for enhancing binding of a pharmaceutical agent to a cell in vitro or in vivo, which method comprises administering to said cell in vitro or in vivo a pharmaceutical composition comprising a pharmaceutical agent and a pharmaceutically acceptable carrier, wherein the pharmaceutically acceptable carrier comprises albumin, and wherein the ratio of albumin to pharmaceutical agent in the pharmaceutical composition is about 18:1 or less. Descriptions of the pharmaceutical composition, pharmaceutical agent, pharmaceutically acceptable carrier, administration routes, and components thereof set forth above in connection with the inventive pharmaceutical composition and inventive method also are applicable to those same aspects of the transport and binding methods.

In the methods for enhancing transport of a pharmaceutical agent to the site of an infirmity or for enhancing binding of pharmaceutical agent to a cell, the pharmaceutically acceptable carrier preferably comprises albumin, most preferably human serum albumin. Not to adhere to any one particular theory, it is believed that the ratio of protein, e.g., human serum albumin, to pharmaceutical agent in the pharmaceutical composition affects the ability of the pharmaceutical agent to bind and transport the pharmaceutical agent to a cell. In this regard, higher ratios of protein to pharmaceutical agent generally are associated with poor cell binding and transport of the pharmaceutical agent, which possibly is the result of competition for receptors at the cell surface. The ratio of protein; e.g., albumin, to active pharmaceutical agent must be such that a sufficient amount of pharmaceutical agent binds to, or is transported by, the cell. Exemplary ranges for protein-drug preparations are protein to drug ratios (w/w) of 0.01:1 to about 100:1. More preferably, the ratios are in the range of 0.02:1 to about 40:1. While the ratio of protein to pharmaceutical agent will have to be optimized for different protein and pharmaceutical agent combinations, generally the ratio of protein, e.g.; albumin, to pharmaceutical agent is about 18:1 or less (e.g., about 15:1, about 10:1, about 5:1, or about 3:1). More preferably, the ratio is about 0.2:1 to about 12:1. Most preferably, the ratio is about 1:1 to about 9:1. Preferably, the formulation is essentially free of cremophor, and more preferably free of Cremophor EL® (BASF). Cremophor EL® is a non-ionic emulsifying agent that is a polyether of castor oil and ethylene oxide. As described above, cremophor typically is used as a solvent for paclitaxel, and is associated with side effects that can be severe (see, e.g., Gelderblom et al., supra).

The pharmaceutical agent can be any suitable pharmaceutical agent described herein (e.g., propofol, paclitaxel, or docetaxel). In addition, the pharmaceutical agent can be a nucleic acid sequence, most preferably a DNA sequence. In this regard, the inventive pharmaceutical composition can be used to transport genes to a cell by way of a receptor mediated/caveolar/vescicular transport. In order to transport DNA sequences, such as genes or other genetic material, including but not limited to plasmids or c-DNA, into a cell (e.g. an endothelial cell or a tumor cell), pharmaceutical compositions comprising albumin in combination with genetic material can be prepared. Since tumor cells and other cells in sites of inflammation have high uptake for proteins, the genetic material is preferentially taken up into these cell types and may be incorporated into the genetic material of the cell for a useful therapeutic effect. The use of proteins, such as human serum albumin, serves as a non-viral vector for the delivery of genetic material without the risk of virus-associated diseases or side effects. For example, a pharmaceutical composition comprising the nucleic acid sequence encoding β-galactosidase or green fluorescent protein (GFP) and albumin can be prepared and contacted with endothelial cells derived from human umbilical vein or human lung microvessels to facilitate incorporation of the nucleic acid sequence into the endothelial cells. Incorporation of the nucleic acid sequence can be detected using methods known in the art, such as, for example, fluorescence or staining.

In the inventive method for enhancing transport of a pharmaceutical agent to the site of an infirmity, the infirmity can be any suitable disease or condition. Preferably, the infirmity is cancer, cardiovascular disease, or arthritis.

In the inventive method for enhancing binding of a pharmaceutical agent to a cell in vitro or in vivo, the pharmaceutical composition is administered to a cell in vitro or in vivo. Desirably, the cell is an animal cell. More preferably the cell is a mammalian cell, and most preferably the cell is a human cell. The pharmaceutical composition preferably is administered to a cell in vivo. The cell can be any suitable cell that is a desirable target for administration of the pharmaceutical composition. For example, the cell can be located in or derived from tissues of the digestive system including, for example, the esophagus, stomach, small intestine, colon, rectum, anus, liver, gall bladder, and pancreas. The cell also can be located in or derived from tissues of the respiratory system, including, for example, the larynx, lung, and bronchus. The cell can be located in or derived from, for example, the uterine cervix, the uterine corpus, the ovary vulva, the vagina, the prostate, the testis, and the penis, which makeup the male and female genital systems, and the urinary bladder, kidney, renal pelvis, and ureter, which comprise the urinary system. The cell, can be located in or derived from tissues of the cardiovascular system, including, for example, endothelial cells and cardiac muscle cells. The cell also can be located in or derived from tissues of the lymphoid system (e.g., lymph cells), the nervous system (e.g., neurons or glial cells), and the endocrine system (e.g., thyroid cells). Preferably, the cell is located in or derived from tissues of the cardiovascular system. Most preferably, the cell is an endothelial cell. In the context of the inventive method for enhancing transport and enhancing binding of a pharmaceutical agent to a cell, the pharmaceutical composition desirably contacts more than one cell.

In another aspect of the invention, the inventive methods for enhancing transport and enhancing binding of a pharmaceutical agent to a cell can be used to treat tumor cells. Tumor cells exhibit an enhanced uptake of proteins including, for example, albumin and transferrin, as compared to normal cells. Since tumor cells are dividing at a rapid rate, they require additional nutrient sources compared to normal cells. Tumor studies of the inventive pharmaceutical compositions containing paclitaxel and human serum albumin showed high uptake of albumin-paclitaxel into tumors. This has been found to be due to the previously unrecognized phenomenon of the albumin-drug transport by glycoprotein 60 ("gp60") receptors, which are specific for albumin.

Thus, in accordance with another aspect of the present invention, the albumin-specific gp60 receptor and other protein transport receptors that are present on tumor cells can be used as a target to inhibit tumor growth. By blocking the gp60 receptor using antibodies against the gp60 receptor or other large or small molecule compounds that bind, block, or inactivate gp60 and other protein transport receptors on tumor cells or tumor endothelial cells, it is possible to block the transport of proteins to these cells and thereby reduce their growth rate and cause cell death. Blocking of this mechanism thus results in the treatment of a subject (e.g., a human) with cancer or another disease. Identification of blocking/binding of the specific protein receptor is done by screening any number of compounds against the isolated gp60 or other receptors, such as gp16 orgp30, or by using a whole cell preparation. In addition, suitable animal models also can be used for this purpose, such as, for example, mice containing "knock-out" mutations of the genes encoding gp60 or caveolin-1, or other proteins that are specific for transport. Thus, method of identification of compounds that block or bind gp60, gp16, gp30, or other protein receptors are within the scope of the invention.

In addition, compounds that block or bind the gp60 receptor or other protein receptors can be used in the treatment of several diseases, including cancer. With respect to the treatment of cancer, the blocking or binding compound may be used as a single agent or in combination with other standard chemotherapy or chemotherapies. For example, it is useful to treat the cancer with conventional chemotherapy, or with the inventive albumin-drug pharmaceutical compositions (which show high accumulation in tumors), followed by compounds that block the transport of proteins to the tumor cell. Blocking compounds can be administered prior to, or in conjunction with, other chemotherapeutic or anticancer agents. Thus, any compounds that can block or bind the gp60 receptor, or other protein receptors, are within the scope of the present invention.

The inventive albumin-drug compositions, such as e.g., albumin paclitaxel, albumin-docetaxel, albumin-epothilone, albumin-camptothecin, or albumin-rapamycin, and others, are useful in the treatment of diseases. It is believed that such drug compositions are effective due to increased receptor mediated transport of the protein-drug composition to the required site, for example a tumor. Without wishing to be bound to any particular theory, the transport of a protein-drug composition by receptor mediated transport resulting in a therapeutic effect is believed to be the mechanism for transport of for example, albumin-paclitaxel compositions to a tumor, as well as albumin paclitaxel and albumin-rapamycin transport across the lung. Transport is effected by the presence of gp60, gp16, or gp30 in such tissues. Accordingly, drugs and protein-drug compositions whose transport to sites of disease, e.g., inflammation (e.g., arthritis) or tumors is associated with gp60, gp16, or gp30 receptors and that result in a therapeutic effect are contemplated as compositions of the present invention.

In accordance with another aspect of the present invention, endothelial cells can be co-cultured with cells having a specific function. Incubation of endothelial cells with other cell types such as islet cells, hepatocytes, neuroendocrine cells, and others allows for required transport of components such as proteins and other beneficial components to these cells. The endothelial cells provide for transport of these components to the cultured cell types in order to simulate in vivo conditions, i.e., where these cell types would normally be in close proximity to endothelial cells and would depend on the endothelial cells for transport of nutrients, growth factors, hormone signals, etc. that are required for their proper function. It has previously not been possible to adequately culture these different cell types and obtain physiological performance when endothelial cells were absent. The presence of endothelial cells in culture with desired cell types allows for differentiation and proper functioning of islets, hepatocytes, or neuroendocrine tissue in vitro or ex vivo. Thus it is found that coculture of endothelial cells with islets results in islets with improved physiological properties e.g.; ability to secrete insulin, when compared with those cultured in the absence of endothelial cells. This tissue can then be used ex vivo or transplanted in vivo to treat diseases caused by lack of adequate cellular function (e.g., diabetes in the case of islet cells, hepatic dysfunction in the case of hepatocytes, and neuroendocrine disorders or pain relief in the case of neuroendocrine cells). Cells originating from other tissues and organs (as described above) may also be cocultured with endothelial cells to provide the same benefit. In addition, the coculture may be utilized to incorporate genetic material into the target cell types. The presence of albumin in these cultures is found to be greatly beneficial.

The following examples further illustrate the invention but, of course, should not be construed as in any way limiting its scope.

EXAMPLE 1

This example demonstrates the preparation of pharmaceutical compositions comprising paclitaxel and albumin. Preparation of paclitaxel-albumin compositions is described in U.S. Pat. Nos. 5,439,686 and 5,916,596, which are incorporated in their entirety by reference. Specifically, 30 mg of paclitaxel was dissolved in 3.0 ml methylene chloride. The solution was added to 27.0 ml of human serum albumin solution (2% w/v). Deferoxamine was added as necessary. The mixture was homogenized for 5 minutes at low RPM (Vitris homogenizer, model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a rotary evaporator, and methylene chloride was rapidly removed at 40° C., at reduced pressure (30 mm Hg) for 20-30 minutes. The resulting dispersion was translucent, and the typical average diameter of the resulting paclitaxel particles was in the range 50-220 ma (Z-average, Malvern Zetasizer). The dispersion was further lyophilized for 48 hrs. The resulting cake could be easily reconstituted to the original dispersion by addition of sterile water or saline. The particle size after reconstitution was the same as before lyophilization.

It should be recognized that the amounts, types and proportions of drug, solvents, proteins used in this example are not limiting in any way. When compared to toxicity of paclitaxel dissolved in cremophor formulations, the inventive pharmaceutical composition containing albumin showed substantially lower toxicity.

EXAMPLE 2

This example demonstrates the preparation of a pharmaceutical composition comprising amiodarone and albumin. 30 mg of amiodarone was dissolved in 3.0 ml methylene chloride. The solution was added to 27.0 ml of human serum albumin solution (1% w/v). Deferoxamine was added as necessary. The mixture was homogenized for 5 minutes at low RPM (Vitris homogenizer, model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a rotary evaporator, and methylene chloride was rapidly removed at 40° C., at reduced pressure (30 mm Hg) for 20-30 minutes. The resulting dispersion was translucent, and the typical average diameter of the resulting amiodarone particles was in the range 50-220 nm (Z-average, Malvern Zetasizer). The dispersion was further lyophilized for 48 hrs. The resulting cake was easily reconstituted to the original dispersion by addition of sterile water or saline. The particle size after reconstitution was the same as before lyophilization.

It should be recognized that the amounts, types and proportions of drug, solvents, proteins used in this example are not limiting in anyway. When compared to toxicity of amiodarone dissolved in tween formulations, the inventive pharmaceutical composition with albumin showed substantially lower toxicity.

EXAMPLE 3

This example demonstrates the preparation of pharmaceutical compositions comprising liothyronine and albumin compositions. Liothyronine (or suitable salt) was dissolved in an aqueous alcoholic solution or alkaline solution at a concentration of 0.5-50 mg/ml. The alcoholic (or alkaline) solution was added to an albumin solution (0.1-25% w/v) and agitated. Agitation was low shear with a stirrer or high shear using a sonicator or a homogenizer. At low concentrations of liothyronine, (5-1000 µg/ml) clear solutions were obtained. As the concentration was increased, a milky stable suspension was obtained. These solutions or suspensions were filtered through a sterilizing filter. Organic solvents were removed by evaporation or other suitable method.

EXAMPLE 4

This example demonstrates the preparation of pharmaceutical compositions comprising rapamycin and albumin 30 mg of rapamycin was dissolved in 2 ml chloroform/ethanol. The solution was then added into 27.0 ml of a human serum albumin solution (3% w/v). The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and solvent was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, proteins used in this example are not limiting in anyway.

EXAMPLE 5

This example demonstrates the preparation of a pharmaceutical composition comprising epothilone B and albumin. 30 mg of epothilone B was dissolved in 2 ml chloroform/ethanol. The solution was then added into 27.0 ml of a human serum albumin solution (3% w/v). Deferoxamine was added as necessary. The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and solvent was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, proteins used in this example are not limiting. When compared to toxicity of epothilone B dissolved in cremophor formulations, the pharmaceutical composition comprising albumin showed substantially lower toxicity.

EXAMPLE 6

This example demonstrates the preparation of pharmaceutical compositions comprising colchicine dimer and albumin. 30 mg of colchicine-dimer was dissolved in 2 ml chloroform/ethanol. The solution was then added into 27.0 ml of human serum albumin solution (3% w/v). Deferoxamine was added as necessary. The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and solvent was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, proteins used in this example are not limiting. When compared to toxicity of the colchicines dimer dissolved in tween, the pharmaceutical composition comprising albumin showed substantially lower toxicity.

EXAMPLE 7

This example demonstrates the preparation of pharmaceutical compositions comprising docetaxel and albumin 30 mg of docetaxel was dissolved in 2 ml chloroform/ethanol. The solution was then added into 27.0 ml of human serum albumin solution (3% w/v). Deferoxamine was added as necessary. The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and solvent was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasizer): The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, and proteins used in this example are not limiting. When compared to toxicity of the docetaxel dissolved in tween/ethanol which is the standard solvent for this drug, the pharmaceutical composition comprising albumin showed substantially lower toxicity.

EXAMPLE 8

This example demonstrates the preparation of pharmaceutical compositions comprising docetaxel and albumin. 150 mg of docetaxel was dissolved in 1 ml ethyl acetate/butyl acetate and 0.5 ml of an oil for example soybean oil or vitamin E oil. Other ratios of solvents and oils were used and these compositions are also contemplated as part of the invention. A small quantity of a negatively charged component was also optionally added, e.g., benzoic acid (0.001%-0.5%) The solution was then added into 27.0 ml of human serum albumin solution (5% w/v). Deferoxamine was added as necessary. The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and solvent was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, proteins used in this example are not limiting. When compared to toxicity of the docetaxel dissolved in tween/ethanol which is the standard solvent for this drug, the pharmaceutical composition comprising albumin showed substantially lower toxicity.

EXAMPLE 9

This example demonstrates the preparation of pharmaceutical compositions comprising a taxane IDN5390 and albumin. 150 mg of IDN5390 was dissolved in 1 ml ethyl acetate/butyl acetate and 0.5 ml of an oil for example soybean oil or vitamin E oil. Other ratios of solvents and oils were used and these compositions are also contemplated as part of the invention. A small quantity of a negatively charged component was also optionally added, e.g., benzoic acid (0.001%-0.5%) The solution was then added into 27.0 ml of human serum albumin solution (5% w/v). Deferoxamine was added as necessary. The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and solvent was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, proteins used in this example are not limiting. When compared to toxicity of the IDN5390 dissolved in tween, the pharmaceutical composition comprising albumin showed substantially lower toxicity.

EXAMPLE 10

This example demonstrates the preparation of pharmaceutical compositions comprising a taxane IDN5109 and albumin. 150 mg of IDN5109 was dissolved in 2 ml chloroform/ethanol. Other ratios of solvents and oils were used and these compositions are also contemplated as part of the invention. A small quantity of a negatively charged component was also optionally added, e.g., benzoic acid (0.001%4.5%) The solution was then added into 27.0 ml of human serum albumin solution (5% w/v). Deferoxamine was added as necessary. The mixture is homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion fOr at least 5 cycles. The resulting system was transferred into a Rotavap and solvent was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasiier). The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, and proteins used in this example are not limiting. When compared to toxicity of the IDN5109 dissolved in tween, the pharmaceutical composition comprising albumin showed substantially lower toxicity.

EXAMPLE 11

This example demonstrates the preparation of a pharmaceutical composition comprising 10-hydroxy camptothecin (10HC) and albumin. 30 mg of 10-HC was dissolved in 2.0 ml. DMF/methylene chloride/soybean oil. The solution was then added into 27.0 ml of a human serum albumin solution (3% w/v). The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and solvent was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization. It should be recognized that the amounts, types and proportions of drug, solvents, proteins used in this example are not limiting in anyway.

EXAMPLE 12

This example demonstrates the preparation of a pharmaceutical composition comprising cyclosporine and albumin 30 mg of cyclosporine was dissolved in 3.0 ml methylene chloride. The solution was then added into 27.0 ml of a human serum albumin solution (1% w/v). The mixture was homogenized for 5 minutes at low RPM (Vitris homogenizer model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and methylene chloride was rapidly removed at 40° C., at reduced pressure (30 mm Hg) for 20-30 minutes. The resulting dispersion was translucent and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization.

EXAMPLE 13

This example demonstrates the preparation of a pharmaceutical composition containing oil and comprising cyclosporine and albumin. 30 mg of cyclosporine was dissolved in 3.0 ml of a suitable oil (sesame oil containing 10% orange oil). The solution was then added into 27.0 ml of a human serum albumin solution (1% v/w). The mixture was homogenized for 5 minutes at low RPM (Vitris homogenizer, model Tempest I.Q.) in order to form a crude emulsion, and then transferred into a high pressure homogenizer (Avestin). The emulsification as performed at 9000-40,000 psi while recycling the emulsion for at least 5 cycles. The resulting dispersion had a typical average diameter in range of 50-220 nm (Z-average, Malvern Zetasizer). The dispersion was used directly or lyophilized for 48 hours by optionally adding a suitable cryoprotectant. The resulting cake was easily reconstituted to the original dispersion by addition of sterile water or saline. It should be recognized that the amounts, types and proportions of drug, solvents, and proteins used in this example are not limiting in anyway.

EXAMPLE 14

This example demonstrates the preparation of a pharmaceutical composition comprising amphotericin and albumin. 30 mg of amphotericin was dissolved in 3.0 ml methyl pyrrolidinone/methylene chloride. The solution was added to 27.0 ml of a human serum albumin solution (1% w/v). The mixture was homogenized for 5 minutes at low RPM (Vitris homogenizer, model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a rotary evaporator, and solvent was rapidly removed at 40° C., at reduced pressure (30 mm Hg) for 20-30 minutes. The resulting dispersion was translucent, and the typical average diameter of the resulting amphotericin particles was between 50-220 nm (Z-average, Malvern Zetasizer). The dispersion was further lyophilized for 48 hrs. The resulting cake could be easily reconstituted to the original dispersion by addition of sterile water or saline. The particle size after reconstitution was the same as before lyophilization. It should be recognized that the amounts, types and proportions of drug, solvents, and proteins used in this example are not limiting in anyway. Addition of other components such as lipids, bile salts, etc., also resulted in suitable formulations.

EXAMPLE 15

This example demonstrates preclinical pharmacokinetics and pharmacodynamics of a pharmaceutical composition comprising albumin and paclitaxel.

Several preclinical pharmacokinetic studies in mice and rats were conducted to evaluate the possible advantages of albumin-paclitaxel pharmaceutical compositions over cremophor-paclitaxel (Taxol) pharmaceutical compositions. These studies demonstrated: (1) that the pharmacokinetics of albumin-paclitaxel in rats was linear, whereas Taxol pharmacokinetics were non-linear with respect to dose, (2) pharmaceutical compositions comprising albumin and paclitaxel exhibited a lower plasma AUC and $C_{max}$, suggesting more rapid distribution of albumin-paclitaxel compositions to tissues compared with Taxol (excretion is similar), (3) pharmaceutical compositions comprising albumin and paclitaxel exhibited a lower $C_{max}$, which possibly accounts for the reduced toxicities associated with peak blood levels relative to Taxol, (4) the half-life of pharmaceutical compositions comprising albumin and paclitaxel exhibited was approximately 2-fold higher in rats and 4-fold higher in tumor bearing mice relative to Taxol, and (5) the metabolism of paclitaxel in pharmaceutical compositions comprising albumin and paclitaxel was slower than in Taxol pharmaceutical compositions. At 24 hours post-injection in rats, 44% of total radioactivity was still associated with paclitaxel for pharmaceutical compositions comprising albumin and paclitaxel, compared to only 22% for Taxol. The ultimate effect of the above pharmacodynamics, i.e., enhanced intra-cellular uptake, prolonged half-life and slower metabolism for pharmaceutical compositions comprising albumin and paclitaxel exhibited resulted in a tumor AUC 1.7-fold higher, tumor $C_{max}$ 1.2-fold higher, and tumor half-life 1.7-fold longer than for Taxol in tumor bearing mice.

EXAMPLE 16

This example demonstrates reduced side effects and reduced toxicity associated with pharmaceutical compositions comprising paclitaxel and albumin.

Due to the unique nature of pharmaceutical compositions comprising paclitaxel and albumin in the absence of cremophor, the toxicity of pharmaceutical compositions comprising paclitaxel and albumin is substantially lower than Taxol. In preclinical studies in mice and rats, a single dose acute toxicity study in mice showed an $LD_{50}$ dose approximately 59 times greater for pharmaceutical compositions comprising paclitaxel and albumin than for Taxol. In a multiple dose toxicity study in mice, the $LD_{50}$ dose was approximately 10-fold greater for pharmaceutical compositions comprising paclitaxel and albumin than for Taxol. A further study evaluated the degree of myelosuppression in rats treated with pharmaceutical compositions comprising paclitaxel and albumin and Taxol. The results showed that at equi-dose, pharmaceutical compositions comprising paclitaxel and albumin produced considerably less myelosuppression in rats than Taxol. In an acute toxicity study in rats, cerebral cortical necrosis or severe neurotoxicity was observed in animals receiving Taxol at 9 mg/kg but was absent in animals receiving a pharmaceutical composition comprising paclitaxel and albumin at a dose of up to 120 mg/kg. Thus the presence of albumin in a pharmaceutical composition comprising paclitaxel results in a substantial reduction in side effects and toxicity when compared to conventional pharmaceutical compositions comprising paclitaxel.

EXAMPLE 17

This example demonstrates the clinical effects of a pharmaceutical composition comprising paclitaxel and albumin in humans.

Clinical studies in over 500 human patients to date provide evidence supporting the reduction in toxicity and side-effects for a pharmaceutical composition comprising paclitaxel and albumin ("albumin-paclitaxel") when compared with cremophor-paclitaxel compositions (Taxol). In a phase I study of 19 patients, the maximum tolerated dose of albumin-paclitaxel given every 3 weeks was 300 mg/m$^2$. This is substantially higher than the generally administered dose of cremophor-paclitaxel which is 175 mg/m$^2$ given once every 3 weeks. The hematological toxicities in these patients were mild with no hypersensitivities, mild neuropathies, and no administration related side effects such as venous irritation, etc.

In another phase I study of 27 patients, the maximum tolerated dose of albumin-paclitaxel given on a weekly schedule was 125-150 mg/m$^2$. This is substantially higher than the generally administered dose of cremophor-paclitaxel which is 80 mg/m$^2$ when given on a weekly schedule. The hematological toxicities in these patients were mild with no hypersensitivities, mild neuropathies, and no administration related side effects such as venous irritation, etc.

In two phase II studies of albumin-paclitaxel given at either 175 or 300 mg/m$^2$ every 3 weeks in 43 and 63 patients respectively, hematological toxicities were low with only 7% and 24% of patients with ANC <500/mm$^3$ at 175 mg/m$^2$ and 300 mg/m$^2$ respectively. Severe neuropathy occurred in 0% and 14% of patients for 175 mg/m$^2$ and 300 mg/m$^2$ respectively. There was no incidence of severe hypersensitivity, and no incidence of administration related side effects such as venous irritation, pain on injection, etc. These side effects were substantially lower than experienced with Taxol.

In phase III trials comparing the albumin-paclitaxel composition ABI-007 against Taxol (which contains cremophor-paclitaxel), the dose of ABI-007 was substantially higher (260 mg/m$^2$ vs. 175 mg/m$^2$ for Taxol) indicating it was better tolerated. The albumin-paclitaxel compositions also demonstrated significantly reduced neutropenia when compared to cremophor-paclitaxel.

EXAMPLE 18

This example demonstrates enhanced preclinical efficacy using a pharmaceutical composition comprising albumin and paclitaxel.

An in vitro cytotoxicity study comparing the effect of albumin-paclitaxel and Taxol on cervical squamous cell carcinoma A431 showed an approximately 4-fold increase in cytotoxic activity for albumin-paclitaxel with an $IC_{50}$ of 0.0038 and 0.012 µg/ml for albumin-paclitaxel and Taxol respectively.

In five different human xenograft tumor models in athymic mice (MX-1 mammary, NCI-H522 lung, SK-OV-3 ovarian, PC-3 prostate, and HT-29 colon), the MTD or equitoxic dose of ABI-007 was 1.5-3.4-fold higher than for Taxol, and resulted in statistically significant improvement in tumor growth delay (p<0.05) in all tumors except the lung tumor (p=0.15).

In the MX 1 mammary model, one hundred percent (100%) of albumin-paclitaxel treated animals survived 103 days, as compared to 20-40% surviving in groups treated with equivalent doses of Taxol.

EXAMPLE 19

This example demonstrates enhanced clinical efficacy using a pharmaceutical composition comprising albumin and paclitaxel administered intra-arterially.

In a Phase I/II Study of intra-arterial administration of a pharmaceutical composition comprising albumin and paclitaxel, as described herein, patients were enrolled for head & neck cancer (N=31) and cancer of the anal canal (N=12). The dose escalated from 120-300 mg/m$^2$ given over 30 minutes by percutaneous superselective intra-arterial infusion, q 3-4 wk. Head and neck cancer patients exhibited a response rate of 76% (N=29), while patients with cancer of the anal canal exhibited a response rate 64% (N=11).

EXAMPLE 20

This example demonstrates the preparation of a pharmaceutical composition containing 3% oil and comprising propofol and albumin.

An oil-in-water emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase was passed through a filter (0.2 um filter). The oil phase was prepared by dissolving egg lecithin (0.4% by weight) and propofol (1% by weight) into soybean oil (3% by weight) at about 50° C.-60° C. and was stirred until dissolved. The oil phase was added to the aqueous phase and homogenized at 10,000 RPM for 5 min. The crude emulsion was high pressure homogenized at 20,000 psi and recirculated for 15 cycles at 5° C. Alternately, discrete passes through the homogenizer were used. The final emulsion was filtered (0.2 µm filter) and stored under nitrogen. The resulting pharmaceutical composition contained the following general ranges of components (weight %): propofol 0.5-5%; human serum albumin 0.5-3%; soybean oil 0.5-3.0%; egg lecithin 0.12-1.2%; glycerol 2.25%; water for injection q.s. to 100; pH 5-8. Suitable chelators, e.g., deferoxamine (0.001-0.1%), were optionally added.

EXAMPLE 21

This example demonstrates the preparation of a pharmaceutical composition containing 5% oil and comprising propofol and albumin.

An oil-in-water emulsion containing 1% (by weight) of propofol was prepared as follows. The aqueous phase was prepared by adding glycerol (2.25% by weight) and human serum albumin (0.5% by weight) into water for injection and was stirred until dissolved. The aqueous phase was passed through a filter (0.2 um filter). The oil phase as prepared by dissolving egg lecithin (0.8% by weight) and propofol (1% by weight) into soybean oil (5% by weight) at about 50° C.-60° C. and was stirred until dissolved. The oil phase was added to the aqueous phase and homogenized at 10,000 RPM for 5 min. The crude emulsion was high pressure homogenized at 20,000 psi and recirculated for 15 cycles at 5° C. Alternately, discrete passes through the homogenizer were used. The final emulsion was filtered (0.2 μm filter) and stored under nitrogen. The resulting pharmaceutical composition contained the following general ranges of components (weight %): propofol 0.5-5%; human serum albumin 0.5-3%; soybean oil 0.5-10.0%; egg lecithin 0.12-1.2%; glycerol 2.25%; water for injection q.s. to 100; pH 5-8. Suitable chelators, e.g., deferoxamine (0.001-0.1%), were optionally added

EXAMPLE 22

This example demonstrates the preparation of a pharmaceutical composition comprising propofol and albumin that is free of oil.

Using the procedure similar to that described in Example 18, propofol compositions containing albumin and tween 80 were prepared. The aqueous phase was prepared by adding glycerol (2.25% by weight), human serum albumin (0.5% by weight), tween 80 (1.5% by weight) and deferoxamine mesylate (0.1% by weight) into water for injection and stirred until dissolved. The aqueous phase was passed through a filter (0.2 μm filter). Propofol (1% by weight) was added to the aqueous phase and homogenized at 10,000 RPM for 5 min. The Crude emulsion was high pressure homogenized at 20,000 psi and recirculated for 15 cycles at 5° C. Alternately, discrete passes through the homogenizer were used. The final emulsion was filtered (0.2 um filter) and stored under nitrogen. The resulting pharmaceutical composition contained the following general ranges of components (weight %): propofol 0.5-5; human serum albumin 0.5-3%; tween 80 0.1-1.5%; deferoxamine mesylate 0.0001-0.1%; glycerol 2.25%; water for injection q.s. to 100; pH 5-8.

EXAMPLE 23

This example demonstrates the preparation of a pharmaceutical composition comprising propofol, albumin, and vitamin E-TPGS, which is free of oil.

Using the procedure similar to that described in Example 19, propofol compositions containing albumin and vitamin E-TPGS were prepared. The aqueous phase was prepared by adding glycerol (2.25% by weight), human serum albumin (0.5% by weight), vitamin E-TPGS (1% by weight) and deferoxamine mesylate (0.1% by weight) into water for injection and was stirred until dissolved. The aqueous phase was passed through a filter (0.2 um filter). Propofol (1% by weight) was added to the aqueous phase and homogenized at 10,000 RPM for 5 min. The crude emulsion was high pressure homogenized at 20,000 psi and recirculated for 15 cycles at 5° C. Alternately, discrete passes through the homogenizer were used. The final emulsion was filtered (0.2 μm filter) and stored under nitrogen. The resulting pharmaceutical composition contained the following general ranges of components (weight %): propofol 0.5-5; human serum albumin 0.5-3%; vitamin E-TPGS 0.5-4.0%; optionally deferoxamine mesylate 0.0001-0.1%; glycerol 2.25%; water for injection q.s. to 100; pH 5-8.

EXAMPLE 24

This example demonstrates the preparation of a pharmaceutical composition comprising propofol, albumin, vitamin E-TPGS, and 1% oil.

An emulsion containing 1% (by weight) of propofol was prepared by the following method. The aqueous phase was prepared by adding glycerol (2.25% by weight) and human serum albumin (0.5% by weight) into water for injection and stirred until dissolved. The aqueous phase was passed through a filter (0.2 μm filter). Surfactant, e.g., Vitamin E-TPGS (0.5%), was added to aq ueous phase. The oil phase consisted of propofol (1% by weight) and 1% soybean oil. The oil phase was added to the aqueous phase and homogenized at 10,000 RPM for 5 min. The crude emulsion was high pressure homogenized at 20,000 csi and recirculated for up to 15 cycles at 5° C. Alternatively, discrete passes through the homogenizer were used. The final emulsion was filtered (0.2 μm filter) and stored under nitrogen.

The resulting pharmaceutical composition contained the following general ranges of components (weight %): propofol 0.5-5%; human serum albumin 0.01-3%; Vitamin E-TPGS 0.1-2%; soybean or other oil (0.1%-5%); glycerol 2.25%; water for injection q.s. to 100; pH 5-8. Deferoxamine was optionally added (0.001%-0.1% by weight).

EXAMPLE 25

This example demonstrates the preparation of a pharmaceutical composition comprising propofol, albumin, vitamin E-TPGS, 1% oil, and a negatively charged component.

An emulsion containing 1% (by weight) of propofol was prepared by the following method. The aqueous phase was prepared by adding glycerol (2.25% by weight) and human serum albumin (0.5% by weight) into water for injection and was stirred until dissolved. The aqueous phase was passed through a filter (0.2 μm filter). Surfactant, e.g., Vitamin E-TPGS (0.5%), was added to aqueous phase. The oil phase consisted of propofol (1% by weight) and 1% soybean oil. A small quantity of negatively charged component (0.001%4%), e.g., a phospholipid or bile salt was added. The oil phase was added to the aqueous phase and homogenized at 10,000 RPM for 5 min. The crude emulsion was high pressure homogenized at 20,000 psi and recirculated for up to 15 cycles at 5° C. Alternatively, discrete passes through the homogenizer were used. The final emulsion was filtered (0.2 μm filter) and stored under nitrogen.

The resulting pharmaceutical composition contained the following general ranges of components (weight %): propofol 0.5-5%; human serum albumin 0.01-3%; Vitamin E-TPGS 0.1-2%; soybean or other oil (0.1%-5%); glycerol 2.25%; water for injection q.s. to 100; pH 5-8. Deferoxamine was optionally added (0.001%-0.1% by weight).

EXAMPLE 26

This example demonstrates the preparation of a pharmaceutical composition comprising propofol, albumin, vitamin E-TPGS, 1% oil, and a negatively charged component (sodium deoxycholate).

An emulsion containing 1% (by weight) of propofol was prepared by the following method. The aqueous phase was prepared by adding glycerol (2.25% by weight) and human serum albumin (0.5% by weight) into water for injection and stirred until dissolved. The aqueous phase was passed through a filter (0.2 μm filter). Surfactant, e.g., Vitamin E-TPGS (0.5%), was added to aqueous phase. The oil phase consisted of propofol (1% by weight) and 1% soybean oil. A small quantity of negatively charged component (0.001%-1%), e.g., sodium deoxycholate was added. The oil phase was added to the aqueous phase and homogenized at 10,000 RPM for 5 min. The crude emulsion was high pressure homogenized at 20,000 psi and recirculated for up to 15 cycles at 5° C. Alternately, discrete passes through the homogenizer were used. The final emulsion was filtered (0.2 μm filter) and stored under nitrogen.

The resulting pharmaceutical composition contained the following general ranges of components (weight %): propofol 0.5-5%; human serum albumin 0.01-3%; Vitamin E-TPGS 0.1-2%; soybean or other oil (0.1%-5%); glycerol 2.25%; water for injection q.s. to 100; pH 5-8. Deferoxamine was optionally added (0.001%-0.1% by weight).

EXAMPLE 27

This example demonstrates the preparation of a pharmaceutical composition comprising propofol, albumin, vitamin E-TPGS, 1% oil, and a negatively charged component (phospholipids, bile salts, polyaminoacids etc).

An emulsion containing 1% (by weight) of propofol was prepared as follows. The aqueous phase was prepared by adding glycerol (2.25% by weight) and human serum albumin (0.5% by weight) into water for injection and stirred until dissolved. The aqueous phase was passed through a filter (0.2 μm filter). Surfactant, e.g., Vitamin E-TPGS (0.5%), was added to aqueous phase. The oil phase consisted of propofol (1% by weight) and 1% soybean oil. A small quantity of negatively charged component (0.001%-1%), e.g., phosphatidyl choline was added. The oil phase was added to the aqueous phase and homogenized at 10,000 RPM for 5 min. The crude emulsion was high pressure homogenized at 20,000 psi and recirculated for up to 15 cycles at 5° C. Alternatively, discrete passes through the homogenizer were used. The final emulsion was filtered (0.2 μm filter) and stored under nitrogen.

The resulting pharmaceutical composition contained the following general ranges of components (weight %): propofol 0.5-5%; human serum albumin 0.01-3%; Vitamin E-TPGS 0.1-2%; soybean or other oil (0.1%-5%); glycerol 2.25%; water for injection q.s. to 100; pH 5-8. Deferoxamine was optionally added (0.001%-0.1% by weight).

EXAMPLE 28

This example demonstrates the binding of propofol to albumin

The binding of propofol to albumin was determined as follows. Solubility of propofol was tested in water and in solutions containing albumin. 250 μL of propofol was added to 10 mL of a water or albumin solution and stirred for 2 hours in a scintillation vial. The solution was then transferred to a 15 mL polyethylene centrifuge tube and kept at 40° C. for about 16 hours. Samples of water and albumin solutions were assayed for propofol. Solubility of propofol in water was determined to be 0.12 mg/ml. Solubility of propofol in albumin solutions was dependent on the concentration of albumin and increased to 0.44 mg/ml when the albumin concentration was 2% (20 mg/ml). The solutions were ultrafiltered through a 30 kD MWCO filter and the filtrates were assayed for propofol. It was found that for the propofol/water solution, 61% of the propofol could be recovered in the filtrate whereas for the propofol/albumin solution, only 14% was recovered in the filtrate, indicating a substantial binding of propofol with albumin. Based on these results, addition of albumin to pharmaceutical compositions comprising propofol result in a decrease in the amount of free propofol due to albumin binding of the propofol.

EXAMPLE 29

This example demonstrates the reduction of free propofol in a pharmaceutical composition by filtration/membrane contact.

As observed in the experiments described in Example 28, filtration or ultrafiltration of pharmaceutical compositions comprising propofol results in a reduction in the amount of free propofol. Diprivan and a pharmaceutical composition prepared in accordance with the present invention containing albumin, each of which contained 1% propofol (10 mg/ml), were ultrafiltered using a 30 kD membrane. The amount of free propofol was measured in the filtrate using HPLC. The concentration of free propofol in the filtrate was about 17 μg/ml for Diprivan, while the concentration of free propofol in the filtrate was about 7 μg/ml for the inventive pharmaceutical composition. The results correspond to an effective reduction of free propofol by greater than a factor of 2 for pharmaceutical composition comprising propofol and albumin

EXAMPLE 30

This example demonstrates administration of a pharmaceutical composition comprising propofol and albumin to humans.

A randomized, double-blind clinical trial was conducted to compare adverse skin sensations of a pharmaceutical composition comprising propofol and albumin with that of a commercially available propofol formulation, Diprivan. Trials were conducted in compliance with Good Clinical Practices and informed consent was taken from the subjects. Adult human subjects of either sex were eligible for participation if they had unbroken, apparently normal skin of dorsal side of their hands.

The formulations originally stored in a refrigerator were brought to room temperature and then 10 μL of the formulations was placed slowly on the back side of both the hands of a subject simultaneously. The overall reaction and feel on their hands for the formulations were noted. The results of this study are set forth in Table 1.

TABLE 1

| | % of subjects with ABI-Propofol sensation | | % of subjects with Diprivan sensation | |
| --- | --- | --- | --- | --- |
| Order of a test on a subject | Mild warm or stinging or biting | No sensation | Mild warm or stinging or biting | No sensation |
| 1st incidence | 0.0 | 100.0 | 75 | 25 |

EXAMPLE 31

This example demonstrates the use of deferoxamine as antioxidant in a pharmaceutical composition comprising propofol.

Pharmaceutical compositions comprising propofol and deferoxamine mesylate, and containing tween or TPGS were stored at 4°, 25°, or 40° C. to test the effect of deferoxamine mesylate in preventing oxidation of propofol. The concentration of propofol was measured for these formulations over time to determine the antioxidant activity of deferoxamine. The data is reported below in Tables 2 and 3 as % potency relative to time zero.

TABLE 2

Albumin/tween formulation

| | 1 month Storage | | |
|---|---|---|---|
| Temp | 4° C. | 25° C. | 40° C. |
| CONTROL | 100% | 88% | 48% |
| 0.01% Def | 101% | 89% | 61% |
| 0.1% Def | 103% | 89% | 64% |

TABLE 3

Albumin/TPGS formulation

| | 1 month Storage | | |
|---|---|---|---|
| Temp | 4° C. | 25° C. | 40° C. |
| CONTROL | 99% | 73% | 42% |
| 0.01% DEF | 99% | 87% | 55% |
| 0.1% DEF | 99% | 85% | 58% |

Under these conditions, deferoxamine was efficient in reducing the level of oxidation of propofol. The effect was more pronounced at higher temperatures. No significant oxidation occurred at 4° C. This study was conducted using stoppers that were not inert or Teflon coated.

EXAMPLE 32

This example demonstrates intrapulmonary delivery of a pharmaceutical composition comprising paclitaxel and albumin (ABI-007).

The purpose of this study was to determine the time course of [$^3$H]ABI-007 in blood and select tissues following intratracheal instillation to Sprague Dawley rats.

The target volume of the intratracheal dose formulation to be administered to the animals was calculated based on a dose volume of 1.5 mL per kg body weight. The dosing apparatus consisted of a Penn-Century microsprayer (Model 1A-1B; Penn-Century, Inc., Philadelphia, Pa.; purchased from DeLong Distributors, Long Branch, N.J.) attached to a 1-mL gas-tight, luer-lock syringe. The appropriate volume of dose preparation was drawn into the dosing apparatus, the filled apparatus was weighed and the weight-recorded. A catheter was placed in the trachea of the anesthetized animal, the microsprayer portion of the dosing apparatus was placed into the trachea through the catheter, and the dose was administered. After dose administration the empty dosing apparatus was reweighed and the administered dose was calculated as the difference in the weights of the dosing apparatus before and after dosing. The average dose for all animals was 4.7738±0.0060 (CV 1.5059) mg paclitaxel per kg body weight.

Blood samples of approximately 250 μL were collected from the indwelling jugular cannulas of JVC rats at the following predetermined post-dosing time points: 1, 5, 10, 15, 30, and 45 minutes (min), and 1, 4, 8, and 24 hours (h). The 24-h blood samples, as well as blood samples collected from animals sacrificed at 10 min, 45 min, and 2 h, were collected via cardiac puncture from anesthetized rats at sacrifice. All blood samples analyzed for total radioactivity were dispensed into pre-weighed sample tubes, and the sample tubes were reweighed, and the weight of each sample was calculated by subtraction. The blood samples collected from the jugular vein as well as the 250-μL aliquots of blood collected from each animal at sacrifice were assayed for total tritium content.

For all rats, the maximum concentration of tritium in blood was observed at 5 min (0.0833 hr) post dosing. The eliraination half-life of tritium, determined over the time interval from 4 h to 24 h, ranged from 19.73 h to 43.02 h. It should be noted that this interval includes only three data points, which may account for the variability in this parameter. The apparent clearance of tritium from blood was on the order of 0.04 L/h. The results of these experiments are set forth below in Table 4.

TABLE 4

Noncompartmental Analysis of Blood Tritium Concentration (mg-eq/L) vs. Time Profiles in Rats After Intratracheal Instillation of [$^3$H]ABI-007

| Parameter | Mean +/− SD |
|---|---|
| $C_{max}$ (mg-eq/L) | 1.615 +/− 0.279 |
| $T_{max}$ (hr) | 0.0833 +/− 0.0 |
| t½beta (hr) | 33.02 +/− 1.99 |
| AUClast (mg-eq × hr/L) | 7.051 +/− 1.535 |
| Cl/F (L/hr) | 0.0442 +/− 0.0070 |
| Fa (Bioavailability) | 1.229 +/− 0.268 |

The mean blood concentration of [$^3$H]ABI-007-derived radioactivity after an intravenous dose to rats was analyzed as a function of time in order to evaluate the bioavailability of tritium derived from an intratracheal dose of [$^3$H]ABI-007. This analysis resulted in a 24-hour AUC (AUClast) of 6.1354 mg-eq □ hr/L. Based on these data, radioactivity derived from the intratracheal dose of [$^3$H]ABI-007 is highly bioavailable. These analyses are based on total radioactivity.

Tritium derived from [$^3$H]ABI-007 is rapidly absorbed after intratracheal instillation. The average absorption and elimination half-lives (k01 half-life and k10 half-life, respectively) for tritium in blood after an intratracheal dose of [$^3$H] ABI-007 (mean+/−SD) were 0.0155+/−0.0058 hr and 4.738+/−0.366 hr, respectively. The average apparent clearance of tritium from blood was 0.1235+/−0.0180 L/hr (see Table 4 above).

Tritium derived from [$^3$H]ABI-007 was absorbed and distributed after intratracheal administration. The time course of tritium in blood was well described by a two-compartment model, with mean absorption and elimination half-lives of 0.0155 and 4.738 hr, respectively. Approximately 28% of the administered dose was recovered in the lung at 10 min after the intratracheal dose. A maximum of less than 1% of the dose was recovered in other tissues, excluding the gastrointestinal tract, at all time points examined.

Based on results from a previously conducted intravenous dose study with [$^3$H]Capxol™, the bioavailability of tritium derived from the intratracheal dose was 1.229±0.268 (mean±SD) for the three animals in this dose group. It should be noted, however, that this estimate of bioavailability is based on total radioactivity. Surprisingly, paclitaxel delivered by the pulmonary route using invention compositions with albumin was rapidly bioavailable indicating excellent transport across pulmonary endothelium. No toxicity in the animals was noted, which was surprising since pulmonary delivery of cytotoxics is known to cause lung toxicities.

A fair amount of radioactivity was present in the gastrointestinal tract (including contents) at 24 hr post dosing (27% for the intratracheal dose). The presence of tritium in the gastrointestinal tract may be due to biliary excretion or clearance of tritium from the respiratory tract via mucociliary clearance with subsequent swallowing.

EXAMPLE 33

This example demonstrates an investigation of Aerotech II and Pari nebulizers for pulmonary delivery of pharmaceutical compositions comprising paclitaxel and albumin.

The study was carried out using the paclitaxel-albumin pharmaceutical composition ABI-007 under the following conditions: room temperature (20-23° C.), relative humidity (48-54%), ambient pressure (629 mmHg), nebulizer flowrate (10 L/min for Aerotech II; 7 L/min for Pari), total flowrate (28.3 L/min), nebulizer pressure drop (23 $lb/in^2$ for Aerotech II; 32 $lb/in^2$ for Pari), run time (15 to 60 seconds), sample volume (1.5 mL), ABI-007 paclitaxel concentration (5, 10, 15 and 20 mg/mL).

Both Aerotech II and Pari nebulizers provided acceptable overall efficiency (30%-60%) when ABI-007 was reconstituted at a concentration range of 5-15 mg/mL. The Pari nebulizer efficiency had higher nebulizer efficiency than the Aerotech II nebulizer. The Pari nebulizer efficiency decreased somewhat as ABI-007 concentration increased. Excellent fine particle fraction was observed (74%-96%). The Aerotech II nebulizer had higher fine particle fraction than the Pari nebulizer. The fine particle fraction was independent of concentration.

The Pari nebulizer delivered 100 mg of paclitaxel in less than 30 minutes using a 15 mg/mL solution of ABI-007. The Aerotech II nebulizer delivered 100 mg of paclitaxel in about 65 min using either a 10 mg/mL or 15 mg/mL solution of ABI-007. Performance stability was tested for both Aerotech II and Pari nebulizers. Aerosol concentration and efficiency of both nebulizers were stable until the drug was exhausted. At 15 mg/mL, the Pari nebulizer consumed the drug at twice the rate of the Aerotech II nebulizer and produced higher aerosol concentrations than that of the Aerotech II nebulizer.

In conclusion, the nanoparticle/albumin formulation of paclitaxel (ABI-007) shows excellent bioavailability in rats when administered by the pulmonary route. There were no overt signs of early toxicity at the administered dose. Pulmonary delivery of nanoparticle paclitaxel (ABI-007) may be achieved using conventional nebulizers.

EXAMPLE 34

This example describes intrapulmonary delivery of pharmaceutical composition comprising albumin and rapamycin. The purpose of this study was to determine the pulmonary absorption of rapamycin in blood following intratracheal instillation to Sprague Dawley rats as compared to intravenous installation.

The target volume of the intratracheal dose formulation that was administered to the animals was calculated based on a dose volume of 1 mL per kg body. The intratracheal dosing apparatus consisted of a Penn-Century microsprayer (Model 1A-1B; Penn-Century, Inc., Philadelphia, Pa.; purchased from DeLong Distributors, Long Branch, N.J.) attached to a 1 mL gas-tight, luer-lock syringe. The appropriate volume of dose preparation was drawn into the dosing apparatus, the filled apparatus was weighed and the weight-recorded. A catheter was placed in the trachea of the anesthetized animal, the microsprayer portion of the dosing apparatus was placed into the trachea through the catheter, and the dose was administered. After dose administration the empty dosing apparatus was reweighed and the administered dose was calculated as the difference in the weights of the dosing apparatus before and after dosing.

250 μL samples were collected from the indwelling jugular cannulas of rats at the following predetermined post-dosing time points: 1, 5, 10, 15, 30, and 45 minutes (min) and 1, 4, 8, and 24 hours (h). All blood samples analyzed were dispensed into pre-weighed sample tubes, and the sample tubes were reweighed, and the weight of each sample was calculated by subtraction. The blood samples collected were assayed for total rapamycin concentration using LC/MS/MS.

Surprisingly, the results showed no significant difference in the blood concentration of rapamycin delivered via pulmonary route versus intravenously. The bioavailability of rapamycin delivered by the pulmonary route using a pharmaceutical composition comprising albumin was calculated to be 109%, indicating excellent transport across pulmonary endothelium.

EXAMPLE 35

This example demonstrates tissue distribution of albumin-rapamycin after intrapulmonary administration of a pharmaceutical composition comprising rapamycin and albumin prepared in accordance with the present invention. The purpose of this study was to determine the pulmonary absorption of rapamycin in tissue following intratracheal instillation to Sprague Dawley rats as compared to intravenous installation.

The target volume of the intratracheal dose formulation that was administered to the animals was calculated based on a dose volume of 1 mL per kg body. The dosing apparatus consisted of a Penn-Century microsprayer (Model 1A-1B; Penn-Century, Inc., Philadelphia, Pa.; purchased from DeLong Distributors, Long Branch, N.J.) attached to a 1-mL gas-tight, luer-lock syringe. The appropriate volume of dose preparation was drawn into the dosing apparatus, the filled apparatus was weighed and the weight-recorded. A catheter was placed in the trachea of the anesthetized animal, the microsprayer portion of the dosing apparatus was placed into the trachea through the catheter, and the dose was administered. After dose administration the empty dosing apparatus was reweighed and the administered dose was calculated as the difference in the weights of the dosing apparatus before and after dosing.

Samples were collected from the brain, lung, and, liver of three rats per group per time point at 10 minutes, 45 minutes, 2 hours, and 24 hours. The samples were collected and analyzed for total rapamycin concentration using LC/MS/MS. The results indicate that rapamycin concentration is greater in lung tissue when delivered via pulmonary as compared to intravenous delivery. However, the total concentration of rapamycin in the brain is lower when delivered via intratracheal (IT) as compared to intravenous (IV). In the liver, there appears to be no difference in the concentration of rapamycin whether delivered IT or IV. Based on these results, pulmonary delivery of rapamycin may be suitable for the treatment of a condition (i.e., lung transplantation), wherein high local concentration of rapamycin would be beneficial.

EXAMPLE 36

This example demonstrates oral delivery of a pharmaceutical composition comprising paclitaxel and albumin (ABI-007).

Tritiated ABI-007 was utilized to determine oral bioavailability of paclitaxel following oral gavage in rats. Following overnight fasting, 5 rats were given 5.5 mg/kg paclitaxel in ABI-007 (Group A) and another 5 rats (Group B) were pretreated with cyclosporine (5.0 mg/kg) followed by 5.6 mg/kg paclitaxel in ABI-007. A pharmacokinetic analysis of blood samples drawn at 0.5, 1, 2, 3, 4, 5, 6, 8, 12, and 24 hours was performed after determination of radioactivity in the blood samples by combustion. Oral bioavailability was determined by comparison with intravenous data previously obtained. The results are set forth below in Table 5.

TABLE 5

Mean AUC 0-24, $C_{max}$, $T_{max}$ and % Absorption of $^3$H-Paclitaxel Derived Radioactivity Following Oral Administration

| Group | Treatment | Dose/Route mg/kg | AUC0-24 (µg eq × hr/mL) | Absorption (%) | Cmax (mg/kg) (µg × eq/mL) | Tmax (hr) |
|---|---|---|---|---|---|---|
| A | ABI-007 in Normal Saline | 5.5/PO(P) | 2.92 | 44.3 | 0.245 | 1 |
| B | ABI-007 in Normal Saline with CsA | 5/PO(C), 5.6/PO(P) | 8.02 | 121.1 | 0.565 | 0.5 |

AUC 0-24 IV (6.06 µg×hr./mL) and IV dose (5.1 mg/kg) were used for calculation of percent absorption (data based on IV dose of ABI-007).

An oral bioavailability of 44% was seen for ABI-007 alone. This is dramatically higher than is seen for other formulations of paclitaxel. The bioavailability increased to 121% when Anima s were treated with cyclosporine (CsA). This is expected as CsA is a known suppressor of the p-glycoprotein pump that would normally prevent absorption of compounds such as paclitaxel from the GI tract. The greater than 100% bioavailability can be explained by reabsorption following biliary excretion of paclitaxel into the GI tract. Other known suppressors or enhancers of absorption may be also utilized for this purpose.

EXAMPLE 37

This example demonstrates improved penetration of paclitaxel into red blood cells and tumor cells upon administration of a pharmaceutical composition comprising paclitaxel and albumin.

Human MX-1 breast tumor fragments were implanted subcutaneously in athymic mice. A pharmaceutical composition comprising paclitaxel and albumin ("paclitaxel-albumin"), as described previously, and Taxol were prepared with $^3$H paclitaxel to a specific activity of 25 µCi/mg paclitaxel. 20 mg/kg radiolabeled paclitaxel-albumin or Taxol was administered intravenously in saline when tumor volume reached approximately 500 mm$^3$. Plasma, blood, and tumor tissue were sampled and analyzed for radioactivity at 5, 15, and 30 minutes and at 1, 3, 8, and 24 hours after administration. Tumor pharmacokinetic (AUC and absorption constant) was analyzed using WinNonlin, Pharsight, USA.

Paclitaxel-albumin exhibited rapid partitioning into red blood cells (RBCs) as shown by a rapid drop of the plasma/ blood radioactivity ratio to unity after intravenous administration of the drug. Complete partitioning into RBCs occurred as early as 1 hr after administration of paclitaxel-albumin. In contrast, the partitioning of paclitaxel formulated as Taxol into RBCs was much slower and was not completed until more than 8 hrs.

Paclitaxel-albumin exhibited a rapid partitioning into tumor tissue with an absorption constant ($K_a$) that was 3.3× greater than Taxol. The $K_a$ were 0.43 hr$^1$ and 0.13 hr$^{-1}$ for paclitaxel-albumin and Taxol, respectively. Rapid uptake of paclitaxel resulted in 33% higher tumor AUC for paclitaxel-albumin than for Taxol. The AUC were 3632 nCi*hr/g and 2739 nCi*hr/g for paclitaxel-albumin and Taxol, respectively.

EXAMPLE 38

This example demonstrates the safety of a pharmaceutical composition comprising paclitaxel and albumin administered to mice.

Athymic mice were treated with escalating doses of paclitaxel-albumin or Taxol everyday for 5 consecutive days. Survival was plotted versus dose to determine the $LD_{50}$. Survival was greatly improved with paclitaxel-albumin versus Taxol (p=0.017, ANOVA). The $LD_{50}$ for paclitaxel-albumin and Taxol were calculated to be 47 mg/kg/day and 30 mg/kg/day for a q1d×5 schedule, respectively. At a dose level of 13.4 mg/kg/day, both paclitaxel-albumin and Taxol were well tolerated with mortality of 1% (1 death out of 72 mice) and 4% (2 deaths out of 47 mice), respectively. At a dose level of 20 mg/kg/clay, there was 1% mortality for paclitaxel-albumin (1 death out of 72 mice) versus 17% mortality for Taxol (8 deaths out of 47 mice) (p=0.0025). At a dose level of 30 mg/kg/day, there was 4% mortality for paclitaxel-albumin (3 deaths out of 72 mice) versus 49% mortality for Taxol (23 deaths out of 47 mice) (p<0.0001).

EXAMPLE 39

This example demonstrates a novel paclitaxel transport mechanism across microvessel endothelial cells (EC) for paclitaxel-albumin compositions.

Nanoparticles and albumin-paclitaxel compositions can accumulate in tumor tissue due to EPR effect resulting from 'leaky' vessels in a tumor. An albumin specific gp60 receptor (albondin) transported albumin across EC by transcytosis of the receptors within caveolae at the cell surface. This transcytosis mechanism allows for the transport of albumin-paclitaxel to the underlying interstitial space. In contrast, cremophor in Taxol inhibited binding of paclitaxel to albumin, greatly reducing paclitaxel transport to the tumor. In addition, the gp16 and gp30 receptors also were involved in intracellular transport of modified albumins containing bound paclitaxel, resulting in increased binding of paclitaxel to endothelial cells with a greater anti-angiogenic effect as compared to Taxol.

EXAMPLE 40

This example demonstrates an increase in endothelial transcytosis of pharmaceutical compositions comprising paclitaxel and albumin as compared to Taxol.

Human lung microvessel endothelial cells (HLMVEC) were grown to confluence on a transwell. The inventive pharmaceutical composition comprising paclitaxel and albumin, or Taxol containing fluorescent paclitaxel (Flutax) at a concentration of 20 µg/mL, was added to the upper transwell chamber.

The transport of paclitaxel by transcytosis from the upper chamber to the lower chamber was monitored continuously using a fluorometer. A control containing only Flutax without albumin was also used. The control with Flutax showed no transport, validating the integrity of the confluent HLMVEC monolayer. Transport of paclitaxel from the albumin-paclitaxel composition was much faster than paclitaxel from Taxol in the presence of 5% HSA (physiological concentration). Transport rate constants ($K_t$) for the albumin-paclitaxel composition and Taxol were 1.396 $hr^{-1}$ and 0.03 $hr^{-1}$, respectively. The total amount of paclitaxel transported across the monolayer was three times higher for the albumin-paclitaxel composition than Taxol.

EXAMPLE 41

This example demonstrates improved endothelial cell (EC) binding by pharmaceutical compositions comprising paclitaxel and albumin as compared to Taxol.

Human umbilical vein endothelial cells (HUVEC) were grown on a 96-well microliter plate. In one experiment, paclitaxel (Flutax-Oregon Green labeled paclitaxel) was reacted with the HUVEC in the presence of increasing concentrations of Cremophor EL/EtOH, which is the vehicle for Taxol. In another experiment, a pharmaceutical composition comprising albumin and Flutax and a Taxol-Flutax composition were reacted to the HUVEC at various final concentrations. Binding of paclitaxel to cells was inhibited by Cremophor. Inhibition was exhibited by an $IC_{50}$ of 0.02% of Cremophor EL/EtOH. This concentration of Cremophor has been shown to persist during Taxol chemotherapy for at least 24 hours. Therefore, it is a relevant process in vivo. At all concentrations tested, a significant amount of paclitaxel from the albumin-paclitaxel composition became bound to cells. In comparison, little or no binding was observed for Taxol.

EXAMPLE 42

This example demonstrates improved albumin binding by pharmaceutical compositions comprising paclitaxel and albumin as compared to Taxol.

Human Serum Albumin (HSA) was immobilized on a plastic ELISA plate, Paclitaxel (Flutax-Oregon Green labeled paclitaxel) was reacted with the immobilized HSA in presence of increasing concentrations of Cremophor EL/EtOH. In another experiment, an albumin-paclitaxel-Flutax composition and a Taxol-Flutax composition were reacted to immobilized HSA at a final concentration of 20 µg paclitaxel/mL. Binding of paclitaxel to albumin was inhibited by Cremophor. Inhibition was exhibited by an $IC_{50}$ of 0.003% of Cremophor EL/EtOH. This concentration of Cremophor has been shown to persist during Taxol chemotherapy for at least 24 hours. Therefore, it is a relevant process in vivo. At a relevant pharmacologic paclitaxel concentration (20 µg/mL), a significant amount of paclitaxel from the albumin-paclitaxel composition became bound to immobilized HSA. In comparison, no binding was observed for Taxol.

EXAMPLE 43

This example demonstrates increased transfer of paclitaxel to albumin for pharmaceutical compositions comprising paclitaxel and albumin as compared to Taxol.

Taxol-Flutax and albumin-paclitaxel-Flutax compositions were mixed with either 5% HSA in Hanks buffer or serum, at 20 µg/mL, 40 µg/ml, and 80 µg/ml. The mixtures were immediately separated on a native 3-14% polyacrylamide gel and the amount of paclitaxel bound to albumin was deterinined by a scanning fluorometer. The transfer of paclitaxel to HSA was more rapid for the albumin-paclitaxel composition versus Taxol. More paclitaxel co-electrophoresed with HSA when either serum or 5% HSA was incubated with the albumin-paclitaxel-Flutax composition or the Taxol-Flutax composition. Upon exposure to 5% HSA, 45%, 60%, and 33% more paclitaxel transferred to HSA for the albumin-paclitaxel-Flutax composition than for the Taxol-Flutax composition, at 20 µg/ml, 40 µg/ml, and 80 µg/ml, respectively. Upon exposure to human serum, 121%, 31%, and 83% more paclitaxel transferred to HSA for the albumin-paclitaxel-Flutax composition than for the Taxol-Flutax composition, at 20 µg/ml, 40 µg/ml, and 80 µg/ml, respectively. The $C_{max}$ for ABI-007 at 260 $mg/m^2$ is approximately 20 µg/mL, therefore this is an important process in vivo.

EXAMPLE 44

This example demonstrates that the glycoprotein receptor gp60 is responsible for binding and transcytosis of albumin-paclitaxel.

Fluorescent labeled paclitaxel (Flutax) albumin compositions were contacted with microvessel endothelial cells in culture. Fluorescent straining was observed under a microscope with evidence of punctuate areas that were postulated to be the gp60 receptor binding the albumin-paclitaxel. This was confirmed by using rhodamine labeled albumin which colocalized with the punctuate fluorescence of paclitaxel.

EXAMPLE 45

This example demonstrates that increasing amounts of albumin can compete with binding of paclitaxel.

Albumin was immobilized on a microtiter plate. Fluorescent paclitaxel was added into the wells and the binding of paclitaxel was measured using a scanning fluorometer. Increasing amounts of albumin were added to the wells and the level of inhibiton of paclitaxel binding to immobilized albumin was measured. The data showed that as the amount of albumin added was increased, a corresponding decrease in binding was seen. A similar effect was seen with binding to endothelial cells. This indicated that higher albumin concentration inhibited binding of paclitaxel. Thus invention compositions having lower amounts of albumin are preferred.

EXAMPLE 46

This example demonstrates that lower amounts of albumin in the inventive pharmaceutical composition results in stable compositions.

To investigate if lower amounts of albumin in compositions would affect stability of the inventive pharmaceutical composition, albumin-paclitaxel compositions with low amounts of albumin were prepared. It was found that these compositions were as stable as compositions with higher quantities of albumin when examined for several months at different temperatures (2-8° C., 25° C. and 40° C.) for potency of paclitaxel, impurity formation, particle size, pH and other typical parameters of stability. Thus compositions with lower amounts of albumin are preferred as this can greatly reduce cost as well as allow increased binding and transport to cells.

EXAMPLE 47

This example demonstrates a pharmaceutical composition comprising albumin and paclitaxel having a high albumin to paclitaxel ratio.

30 mg of paclitaxel was dissolved in 3.0 ml methylene chloride. The solution was added to 27.0 ml of human serum albumin solution (3% w/v) (corresponding to a ratio of albumin to paclitaxel of 27). Deferoxamine was added as necessary. The mixture was homogenized for 5 minutes at low RPM (Vitris homogenizer, model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a rotary evaporator, and methylene chloride was rapidly removed at 40° C., at reduced pressure (30 mm Hg) for 20-30 minutes. The resulting dispersion was translucent, and the typical average diameter of the resulting paclitaxel particles was in the range 50-220 nm (Z-average, Malvern Zetasizer). The dispersion was further lyophilized for 48 hrs. The resulting cake was easily reconstituted to the original dispersion by addition of sterile water or saline. The particle size after reconstitution was the same as before lyophilization.

It should be recognized that the amounts, types and proportions of drug, solvents, proteins used in this example are not limiting in any way. When compared to toxicity of paclitaxel dissolved in cremophor formulations, the inventive pharmaceutical composition containing albumin showed substantially lower toxicity.

EXAMPLE 48

This example demonstrates a pharmaceutical composition comprising albumin and paclitaxel having a low albumin to paclitaxel ratio.

Specifically, 300 mg of paclitaxel was dissolved in 3.0 ml methylene chloride. The solution was added to 27 ml of human serum albumin solution (5% w/v). (corresponding to a ratio of albumin to paclitaxel of 4.5). Deferoxamine was added as necessary. The mixture was homogenized for 5 minutes at low RPM (Vitris homogenizer, model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a rotary evaporator, and methylene chloride was rapidly removed at 40° C., at reduced pressure (30 mm Hg) for 20-30 minutes. The resulting dispersion was translucent, and the typical average diameter of the resulting paclitaxel particles was in the range 50-220 nm (Z-average, Malvern Zetasizer). The dispersion was further lyophilized for 48 hrs. The resulting cake was easily reconstituted to the original dispersion by addition of sterile water or saline. The particle size after reconstitution was the same as before lyophilization.

It should be recognized that the amounts, types and proportions of drug, solvents, proteins used in this example are not limiting in any way. When compared to toxicity of paclitaxel dissolved in cremophor formulations, the inventive pharmaceutical composition containing albumin showed substantially lower toxicity.

EXAMPLE 49

This example demonstrates a pharmaceutical composition comprising albumin and paclitaxel having an intermediate albumin to paclitaxel ratio.

Specifically, 135 mg of paclitaxel was dissolved in 3.0 ml methylene chloride. The solution was added to 27 ml of human serum albumin solution (5% w/v). Deferoxamine was added as necessary. The mixture was homogenized for 5 minutes at low RPM (Vitris homogenizer, model Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a rotary evaporator, and methylene chloride was rapidly removed at 40° C., at reduced pressure (30 mm Hg) for 20-30 minutes. The resulting dispersion was translucent, and the typical average diameter of the resulting paclitaxel particles was in the range 50-220 nm (Leverage, Malvern Zetasizer). The dispersion was further lyophilized for 48 hrs. The resulting cake was easily reconstituted to the original dispersion by addition of sterile water or saline. The particle size after reconstitution was the same as before lyophilization. The calculated ratio (w/w) of albumin to paclitaxel in this invention composition is approximately 10.

It should be recognized that the amounts, types and proportions of drug, solvents, proteins used in this example are not limiting in any way. When compared to toxicity of paclitaxel dissolved in cremophor formulations, the inventive pharmaceutical composition containing albumin showed substantially lower toxicity.

EXAMPLE 50

This example demonstrates the treatment of rheumatoid arthritis in an animal model with an albumin-paclitaxel composition.

The collagen induced arthritis model in the Louvain rat was used to test the therapeutic effect of albumin-paclitaxel composition on arthritis. The paw sizes of the experimental animals were monitored to evaluate the seriousness of arthritis.

After the arthritis was fully developed (usually ~9-10 days after collagen injection), the experimental animals were divided into different groups to receive either albumin-paclitaxel 1 mg/kg q.o.d, or albumin paclitaxel 0.5 mg/kg+prednisone 0.2 mg/kg q.o.d. (combination treatment) intraperitoneally for 6 doses, then one dose per week for three weeks. The paw sizes were measured at the beginning of treatment (day 0) and every time the drug was injected. One group received only normal saline as control. By the end of the experiment, the group receiving albumin-paclitaxel achieved a 42% reduction: of paw size, the combination treatment group showed a 33% reduction of the paw size, while the control group had about 20% increase of the paw size relative to the time when the treatment was initiated.

In conclusion, the albumin-paclitaxel compositions demonstrated therapeutic effect on arthritis. The albumin-paclitaxel combinations are likely to localize at sites of arthritic lesions by transport through receptor-mediated mechanisms like gp60.

EXAMPLE 51

This example demonstrates the use of albumin-paclitaxel compositions to treat cardiovascular restenosis.

Paclitaxel eluting stents in animals cause incomplete healing and, in some instances, a lack of sustained suppression of neointimal growth in the arteries. The present study tested the efficacy of a novel systemic delivery albumin-paclitaxel invention compositions for reducing in-stent restenosis.

Saline-reconstituted albumin-paclitaxel was tested in 38 New Zealand White rabbits receiving bilateral iliac artery stents. Doses of albumin-paclitaxel (1.0 to 5.0 mg/kg paclitaxel dose) were administered as a 10-minute intra-arterial infusion; control animals received vehicle (0.9% normal saline).

In a follow-up chronic experiment, albumin-paclitaxel 5.0 mg/kg was given at stenting with or without an intravenous 3.5-mg/kg repeatalbumin-paclitaxel dose at 28 days; these studies were terminated at 3 months. At 28 days, mean neointimal thickness was reduced (p<3.02) by doses of albumin-paclitaxel >=2.5 mg/kg with evidence of delayed healing. The efficacy of a single dose of albumin-paclitaxel 5.0 mg/kg, however, was lost by 90 days. In contrast, a second repeat dose of albumin-paclitaxel 3.5 mg/kg given 28 days after stenting resulted in sustained suppression of neointimal thickness at 90 days (p<=0.009 versus single dose albumin-paclitaxel 5.0 mg/kg and controls) with nearly complete neointimal healing.

Although systemic albumin-paclitaxel reduces neointimal growth at 28 days, a single repeat dose was required for sustained neointimal suppression. Thus, the inventive composition is suitable for treatment of cardiovascular diseases such as restenosis. Inventive compositions comprising pharmaceutical agents other than paclitaxel, for example rapamycin, other taxanes, epothilones etc, are all suitable for treatment of restenosis in blood vessels or artificial blood vessel grafts such as those used for arterio-venous access in patients requiring hemodialysis.

What is claimed is:

1. A method of treating bladder cancer in a human individual, comprising injecting into the individual an effective amount of a pharmaceutical composition comprising paclitaxel and a pharmaceutically acceptable carrier, wherein the pharmaceutically acceptable carrier comprises albumin, wherein the albumin and the paclitaxel in the composition are formulated as particles, wherein the particles in the composition have a particle size of less than about 200 nm, and wherein the weight ratio of albumin to paclitaxel in the composition is about 1:1 to about 9:1.

2. The method of claim 1, wherein the albumin is human serum albumin.

3. The method of claim 1, wherein the ratio (w/w) of the albumin to the paclitaxel in the pharmaceutical composition is 1:1 to 9:1.

4. The method of claim 1, wherein the ratio (w/w) of the albumin to the paclitaxel in the pharmaceutical composition is about 9:1.

5. The method of claim 2, wherein the ratio (w/w) of the albumin to the paclitaxel in the pharmaceutical composition is 1:1 to 9:1.

6. The method of claim 2, wherein the ratio (w/w) of the albumin to the paclitaxel in the pharmaceutical composition is about 9:1.

7. The method of claim 1, wherein the pharmaceutical composition is injected intravenously.

8. The method of claim 2, wherein the pharmaceutical composition is injected intravenously.

9. The method of claim 3, wherein the pharmaceutical composition is injected intravenously.

10. The method of claim 4, wherein the pharmaceutical composition is injected intravenously.

11. The method of claim 5, wherein the pharmaceutical composition is injected intravenously.

12. The method of claim 6, wherein the pharmaceutical composition is injected intravenously.

* * * * *